United States Patent
Barabas et al.

(10) Patent No.: US 12,371,679 B2
(45) Date of Patent: *Jul. 29, 2025

(54) TRANSFECTION METHOD USING A SLEEPING BEAUTY TRANSPOSASE VARIANT WITH INCREASED SOLUBILITY THAT TRANSFECTS A TARGET CELL WHEN USED IN PROTEIN FORM

(71) Applicant: European Molecular Biology Laboratory, Heidelberg (DE)

(72) Inventors: Orsolya Barabas, Gaiberg (DE); Irma Querques, Zurich (CH); Cecilia Ines Zuliani, Heidelberg (DE)

(73) Assignee: European Molecular Biology Laboratory (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/650,206

(22) Filed: Apr. 30, 2024

(65) Prior Publication Data

US 2024/0287480 A1      Aug. 29, 2024

Related U.S. Application Data

(63) Continuation of application No. 17/817,801, filed on Aug. 5, 2022, which is a continuation of application No. 16/640,976, filed as application No. PCT/EP2018/072320 on Aug. 17, 2018, now Pat. No. 11,441,132.

(30) Foreign Application Priority Data

Aug. 21, 2017   (EP) .................................... 17187128

(51) Int. Cl.
    *C12N 9/12*      (2006.01)
(52) U.S. Cl.
    CPC .................. *C12N 9/1241* (2013.01)
(58) Field of Classification Search
    None
    See application file for complete search history.

(56) References Cited

U.S. PATENT DOCUMENTS

| | | | |
|---|---|---|---|
| 9,228,180 B2 | 1/2016 | Izsvak et al. | |
| 9,840,696 B2 | 12/2017 | Izsvak et al. | |
| 11,441,132 B2* | 9/2022 | Barabas ............... | C12N 9/1241 |
| 2005/0003542 A1 | 1/2005 | Kay et al. | |
| 2017/0226531 A1 | 8/2017 | Craig | |
| 2018/0051265 A1 | 2/2018 | Cooper et al. | |

FOREIGN PATENT DOCUMENTS

| | | |
|---|---|---|
| CN | 101123981 A | 2/2008 |
| CN | 102421902 A | 4/2012 |
| EP | 2025748 A1 | 2/2009 |
| WO | 2009/003671 A2 | 1/2009 |
| WO | 2017/046259 A1 | 3/2017 |

OTHER PUBLICATIONS

Voigt et al., "Sleeping Beauty transposase structure allows rational design of hyperactive variants for genetic engineering", Nature Communications, 7, 11126, 8 pages, Mar. 30, 2016.
Jin et al., "The hyperactive Sleeping Beauty transposase SB100X improves the genetic modification of T cells to express a chimeric antigen receptor", Gene Ther. Sep. 2011; 18(9): 849-856, available online at https://www.ncbi.nlm.nih.gov/pmc/articles/PMC4083583/.
Geurts et al.., "Gene transfer into genomes of human cells by the sleeping beauty transposon system", Molecular Therapy, Academic Press, US, vol. 8, No. 1, pp. 108-117, Jul. 1, 2003.
Fletcher et al., "Enhanced Transposition Activities of Mutant Sleeping Beauty Transposases", Molecular Therapy, vol. 9, No. 1, pp. 178-179, May 1, 2004.
"Amphibians transposase sequence, Seq ID 31.", XP002776513, retrieved from EBI accession No. CSP: AXV14499 Database accession No. AXV14499, Apr. 1, 2010 (1 page).
"Hypophthalmichthys molitrix Thm3 transposase, SEQ ID 24.", XP002776514, retrieved from EBI accession No. GSP: BBF14943 Database accession No. BBF14943 sequence.
International Search Report and Written Opinion, International Patent Application No. PCT/EP2018/072320, Oct. 4, 2018 (16 pages).
Chica et al., Curr Opin Biotechnol. Aug. 2005; 16(4):378-84. (Year: 2006).
Singh et al., Curr Protein Pet Sci. 2017, 18, 1-11 (Year: 2017).
Bornscheuer et al., Curr Protoc Protein Sci. Nov. 2011; Chapter 26: Unit 26.7. (Year: 2011).
Cui et al. J Mol Biol. May 17, 2002; 318 (5): 1221-35 (Year: 2002).
Grabundzija et al. Nucleic Acids Res. Feb. 1, 2013; 41 (3): 1829-47 (Year: 2013).
Alignment of SEQ ID No. 7 of US20180051265 to SEQ ID No. {2 (Year: 2018).
Querques et al., "A highly soluble Sleeping Beauty transposase improves control of gene insertion", Nat Biotechnol. Dec. 2019 ; 37(12): 1502-1512, vailable in Nat Biotechnol Author manuscript in PMC May 4, 2020, 33 pages.

* cited by examiner

*Primary Examiner* — Christian L Fronda
(74) *Attorney, Agent, or Firm* — MORRISON & FOERSTER LLP

(57) ABSTRACT

The present invention relates to improved transposase polypeptides having increased solubility. The enzyme of the invention was developed based on the Sleeping Beauty (SB) transposase. The invention provides further nucleic acids, vectors and recombinant cells encoding or containing the improved transposase, as well as a transposase system. Furthermore provided are medical and non-medical uses of the transposase of the invention for gene delivery. The invention is in particular useful as a tool for gene delivery in genetically modified cell based therapeutic approaches for treating various diseases.

24 Claims, 20 Drawing Sheets

Specification includes a Sequence Listing.

Fig. 4

| Single insertions sequence | Chromosome |
|---|---|
| tgtataatatataTACAGTTGAAGTC | 1 |
| gacacatacacaTACAGTTGAAGTC | 9 |
| ctgttggatgcctcTACAGTTGAAGTC | 7 |
| gatatacatatgTACAGTTGAAGTC | 17 |
| gtactgagtgtatgTACAGTTGAAGTC | 9 |
| cttccggaacaaaTACAGTTGAAGTC | 17 |
| tcaactcagaaatgTACAGTTGAAGTC | 1 |
| ggacacatacatacaTACAGTTGAAGTC | 9 |
| gtactgagtgtatgTACAGTTGAAGTC | 9 |
| tttcaggaacaaTACAGTTGAAGTC | 17 |
| actctcctatgataTACAGTTGAAGTC | 2 |
| actctcctatgataTACAGTTGAAGTC | 2 |
| aataaatgcagttaTACAGTTGAAGTC | 19 |
| atggcgagttaacaTACAGTTGAAGTC | 12 |
| taitccaatgcaaTACAGTTGAAGTC | 6 |
| tatagctaacaataTACAGTTGAAGTC | 1 |
| gcaagtactgcaTACAGTTGAAGTC | 12 |
| ttaaatggaataaTACAGTTGAAGTC | 12 |
| gacacatacacaTACAGTTGAAGTC | 9 |
| aaagcaatagaacaTACAGTTGAAGTC | 17 |
| ttgtataatcataTACAGTTGAAGTC | 6 |
| tatagctaacaataTACAGTTGAAGTC | 1 |
| cctaaatcatcactTACAGTTGAAGTC | 1 |
| ttgtataaatcataTACAGTTGAAGTC | 6 |
| catgtcacatgaagTACAGTTGAAGTC | 5 |
| agtcaggttaacaTACAGTTGAAGTC | 22 |
| ctatttggaaacaTACAGTTGAAGTC | 1 |

| Double insertions sequence | Chromosome |
|---|---|
| catgtcacatgaagTACAGTTGAAGTC------GACTTCAACTGTAcattagttaccac | 5 |
| attgtataaatcataTACAGTTGAAGTC------GACTTCAACTGTAtctacatattcata | 6 |
| tcttttgttgcataTACAGTTGAAGTC------GACTTCAACTGTAgtgatgcatttctg | 13 |
| cccctcctacacaTACAGTTGAAGTC------GACTTCAACTGTAcattatactactaa | X |

| red = left IR |
| blue = right IR |

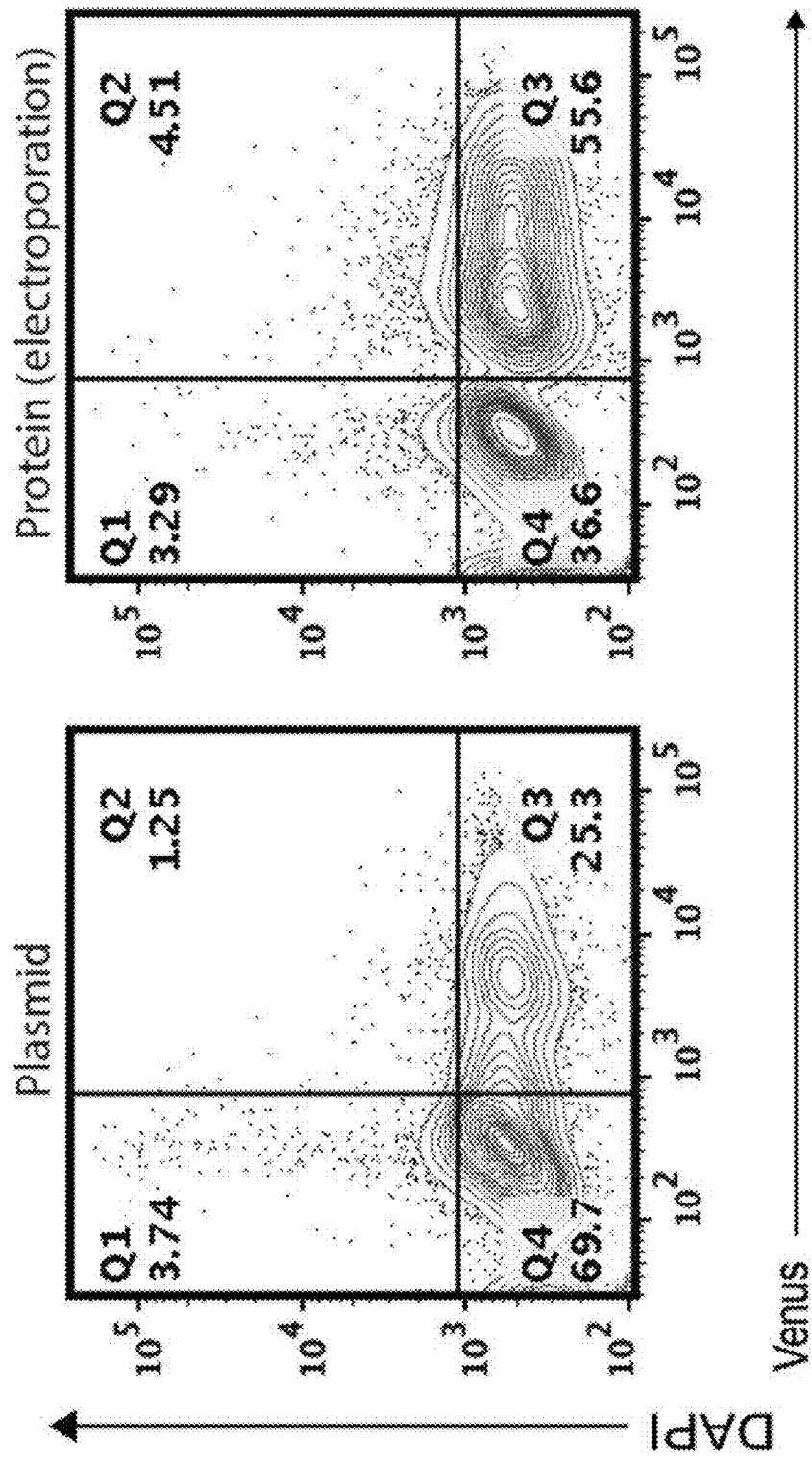

Fig. 10

| hsSB protein (μg) | 0 | 5 | 10 | 20 | Venus+ cells 21 days after electroporation (%) |
|---|---|---|---|---|---|
| HeLa cells | 0 ± 0 | 38.5 ± 9 | 42 ± 1.4 | 45 ± 5.7 | |
| CHO cells | 0 ± 0 | 39.5 ± 6.4 | 50.5 ± 4.9 | 73 ± 0 | |
| mESCs | 0 ± 0 | 4 ± 0 | 10 ± 7.1 | 18 ± 1.4 | |

TRANSFECTION METHOD USING A SLEEPING BEAUTY TRANSPOSASE VARIANT WITH INCREASED SOLUBILITY THAT TRANSFECTS A TARGET CELL WHEN USED IN PROTEIN FORM

FIELD

The present invention relates to improved transposase polypeptides having increased solubility. The enzyme of the invention was developed based on the Sleeping Beauty (SB) transposase. The invention provides nucleic acids, vectors and recombinant cells encoding or containing the improved transposase, as well as a transposase system. Furthermore provided are medical and non-medical uses of the transposase of the invention for gene delivery. The invention is useful as a tool for gene delivery in genetically modified cell based therapeutic approaches for treating various diseases.

BACKGROUND OF THE INVENTION

DNA transposons are discrete genetic entities ubiquitously spread across the tree of life that can move within and between genomes. They are prominent evolutionary forces fostering genome remodeling, evolutionary changes, transmission of antibiotic resistance determinants, and the development of new biological functions such as adaptive immunity. Due to their natural properties, DNA transposons have been successfully utilized as artificial gene carriers and insertional mutagens in transgenesis and functional genomics.

The use of DNA transposons for genome manipulations in vertebrates was first implemented using Sleeping Beauty (SB) transposon from the genomes of salmonid fish. The SB transposon system in current use is a binary system that consists of two components, a gene of interest (genetic cargo) flanked by the specific SB inverted repeats (IRs), and the transposase protein expressed from a separate plasmid or locus. The transposase specifically binds to the IRs, cuts the transposon from a donor locus and integrates it in a new genomic location. SB has exceptionally high insertion efficiency in vertebrate genomes, which has allowed its development into a prime genetic tool, successfully applied in transgenesis of higher organisms, stem cell generation and cancer gene discovery.

SB is now also applied as non-viral gene delivery vector in a number of clinical trials five of which aim to ex vivo modify T cells by incorporating a chimeric antigen receptor (CAR) against malignancy-specific antigens. In these studies, the SB transposase inserts a CAR gene-carrying transposon from a donor plasmid into the genome of patient-derived T cells, which are successively re-infused in the cancer patient. The introduced CARs provide the T cells with new specificities to distinctively target the cancer cells and trigger effector functions upon antigen encounter. Some successful CAR-T therapies target the CD19 antigen that is overexpressed in malignant B cells. This therapy has shown unprecedented response rates (70%-90%) in the treatment of acute and chronic leukemia and will likely enter mainstream care for many B cell malignancies in the next years. However, for the treatment of large number of patients, there is a pressing need to improve manufacturing feasibility and safety, which are also critical requirements of gene therapy in general.

SUMMARY OF THE INVENTION

This disclosure provides an improved technology for inserting a transgene into the genome of a living host cell. A sleeping beauty (SB) transposase is used in protein form rather than as a vector. This was made possible by using rational mutagenesis in a particular region of the SB crystal structure to develop variant SB transposase that is more soluble in protein form. The changes increase solubility while maintaining transposase activity, thereby adapting the variant transposase for the purpose of promoting recombinant integration of a transgene into a target cell when used in protein form rather than as a polynucleotide vector. The transposase is highly soluble in electroporation buffer and thermostable during storage. When introduced into a host cell, it promotes integration of a transgene into the genome of the cell in a dose-dependent manner. The protein is degraded within 48 hours from when it is introduced into the host cell, thereby rapidly clearing transposase activity from the host cell.

A variant SB transposase of this disclosure with improved solubility may have at least two mutated amino acids between amino acid 150 and 250 of the SBX100 sequence. At least one mutated amino acids may be between amino acids 170 to 180 of SEQ. ID NO: 2, with at least one mutated amino acid is between 207 to 217 of SEQ. ID NO: 2. For example, there may be mutated amino acids at positions 172 and 212, both changed to a serine residue. Effective variants are shown in SEQ. ID NO: 1 (referred to herein as hsSB) and SEQ. ID NO: 3.

Other aspects of the invention are put forth in the description below and in the accompanying drawings.

Figure 1A:
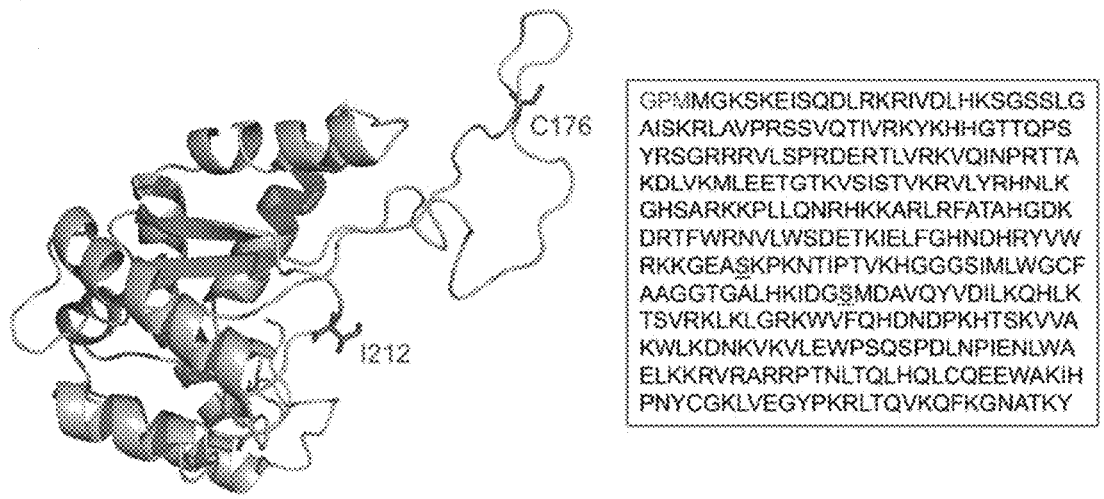
FIGS. 1(A) to 1(I) provide an overview of rational mutagenesis of the SB100X transposase to increase solubility of the encoded protein.

The left side of FIG. 1(A) shows the crystal structure of the native SB100X transposase with its catalytic domain. The right side is the amino acid sequence of the full length hsSB transposase variant protein used for recombinant protein production.

Figure 1B:
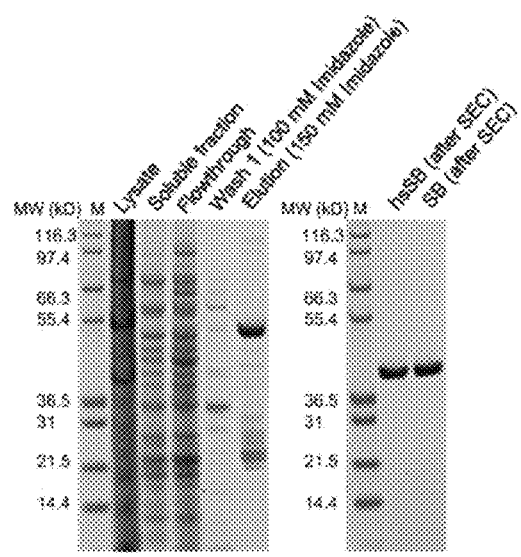
Figure 1C:
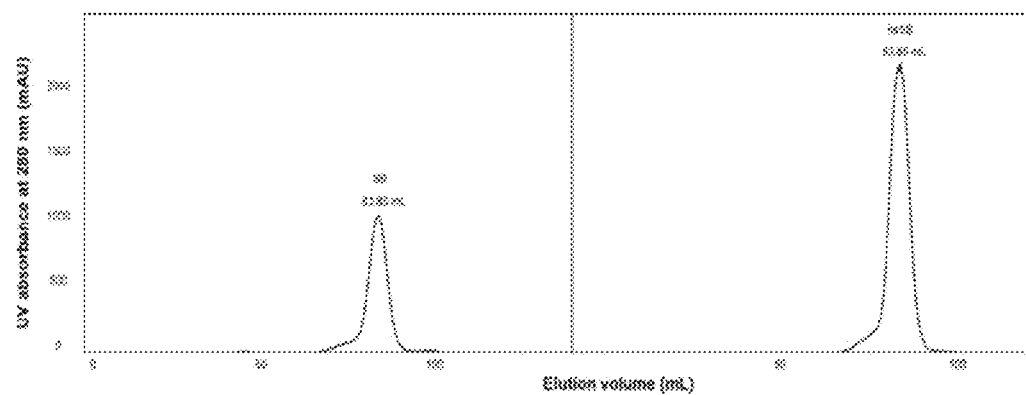
Figure 1D:
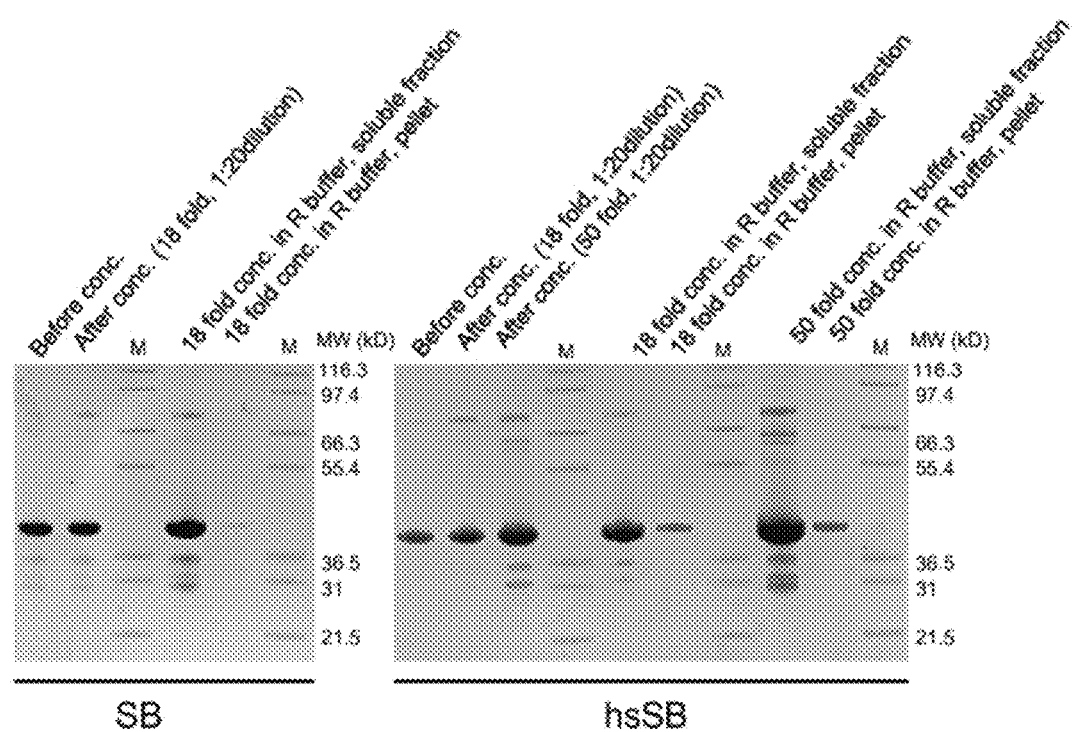
Figure 1E:
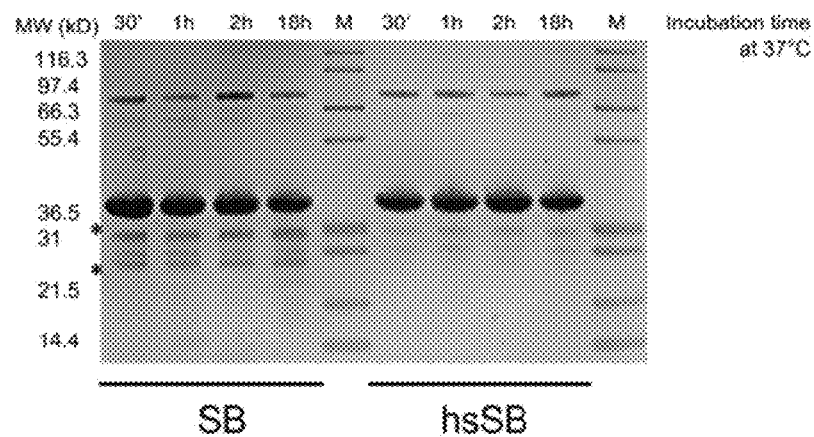

FIG. 1(B) shows SDS-PAGE analysis of the recombinantly produced hsSB protein. FIG. 1(C) is a size exclusion chromatogram showing that hsSB is recombinantly produced at roughly double amounts compared with native SB. FIG. 1(D) demonstrates solubility of hsSB in electroporation buffer. hsSB can be concentrated up to 50 fold (corresponding to 20 mg/mL), whereas native SB undergoes precipitation at concentrations higher than 7 mg/mL. FIG. 1(E) shows SDS-PAGE analysis of purified SB proteins upon incubation at 37° C.

Figure 1F:
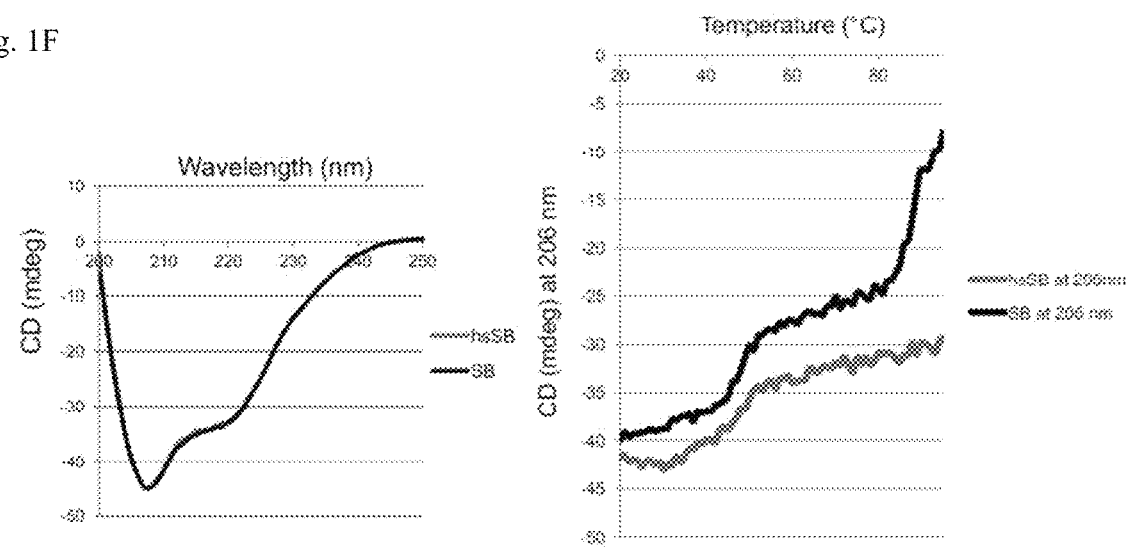

FIG. 1(F) is circular dichroism (CD) data for hsSB, comparing hsSB with native SB. Data in the left panel show that hsSB has the same fold as native SB. However, the right panel shows that hsSB is significantly more thermostable than native SB: it still does not completely unfold at 95° C.

Figure 1G:
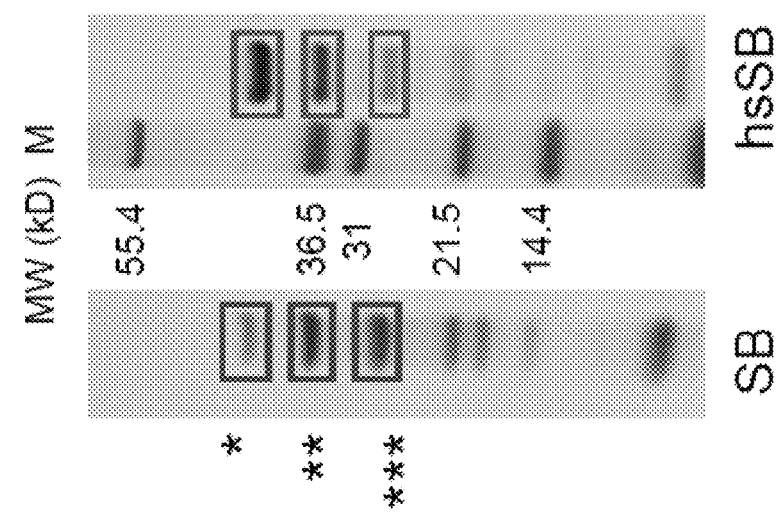
Figure 1G:
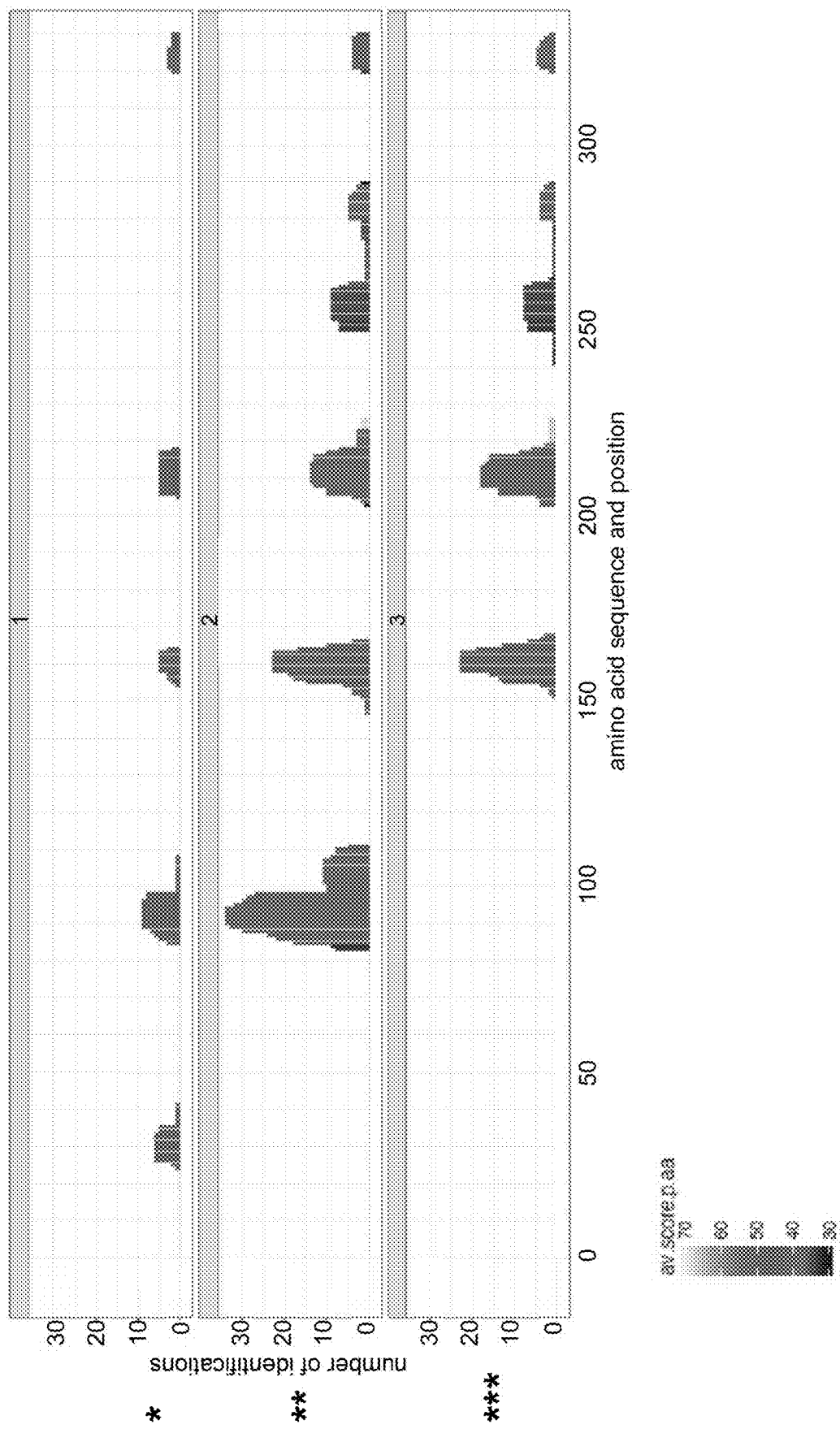

FIG. 1(G) provides data demonstrating that upon long-term storage hsSB is better preserved than SB. The SDS-PAGE analysis shows that native SB undergoes significant degradation after freezing, while hsSB does not. Mass spectrometry analysis (second page) confirmed that the bands correspond to degradation products of the native SB protein.

Figure 2:
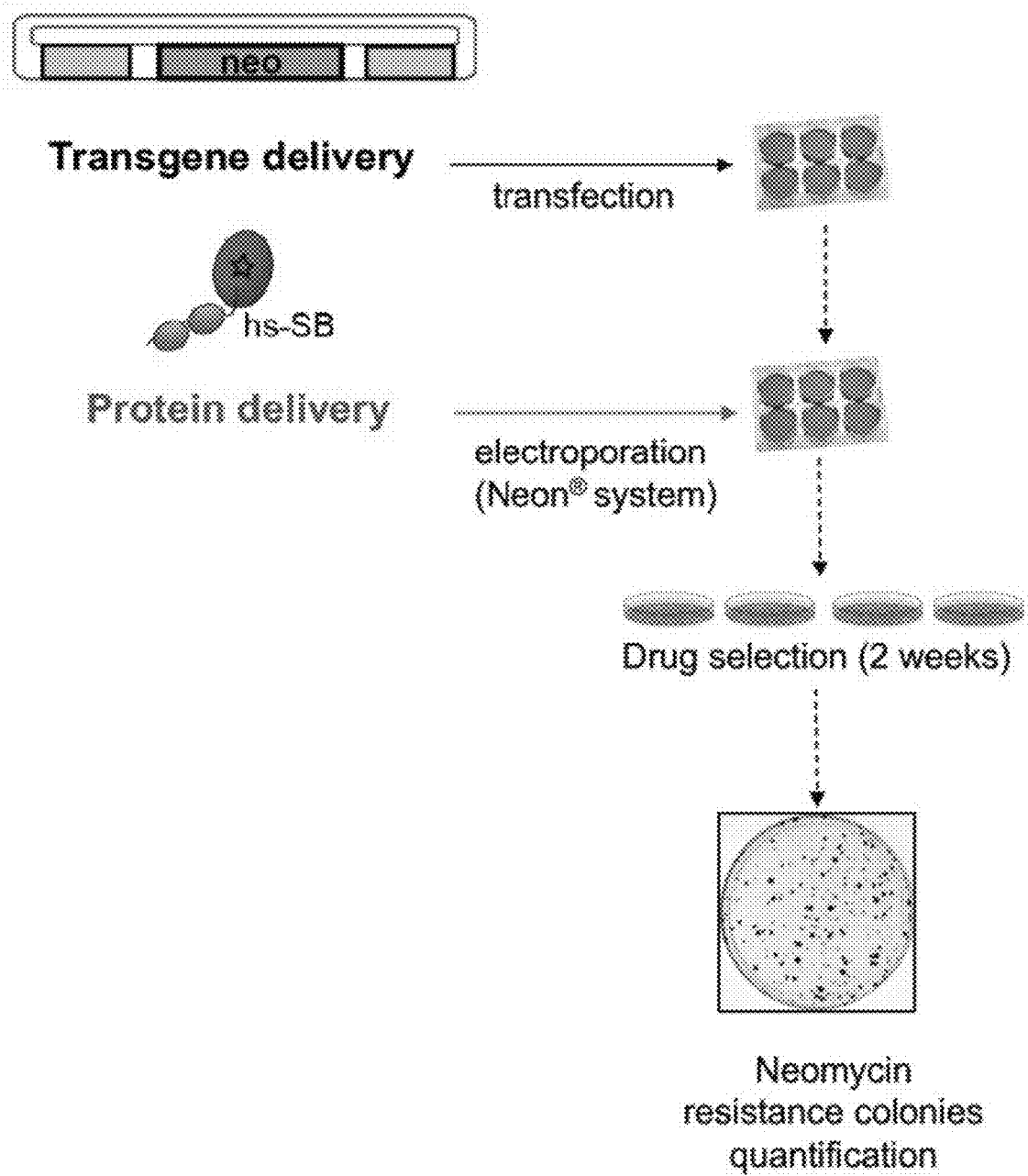

FIG. 2 is a schematic representation of the SBprotAct engineering procedure in which the adapted hsSB is used to integrate a transgene into a host cell.

Figure 3:
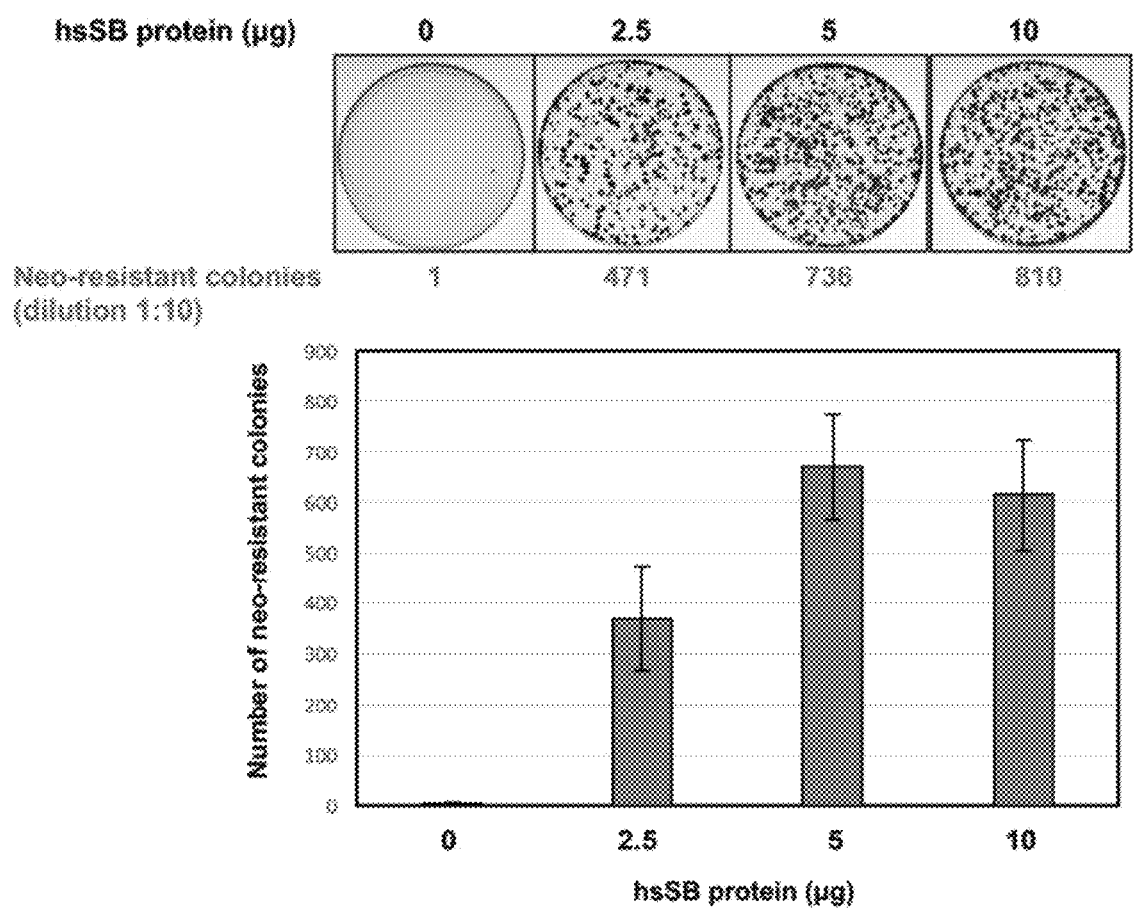

FIG. 3 provides data showing that transgene (neomycin) insertions are driven by transposition activity of the transfected hsSB transposase.

FIG. 4 shows insertion sites derived by sequence analysis of the neomycin locus from 11 isolated neomycin positive HeLa cell clones. Insertions of SB IRs correctly occur at TA dinucleotides.

Figure 5:
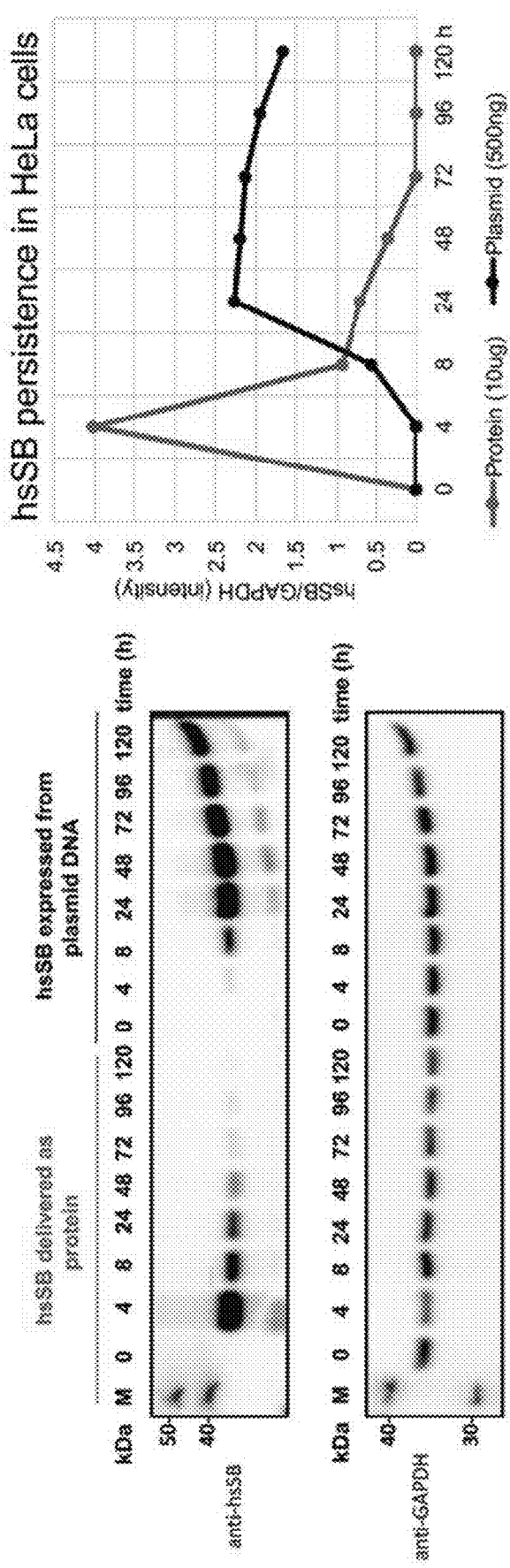
Figure 5B:
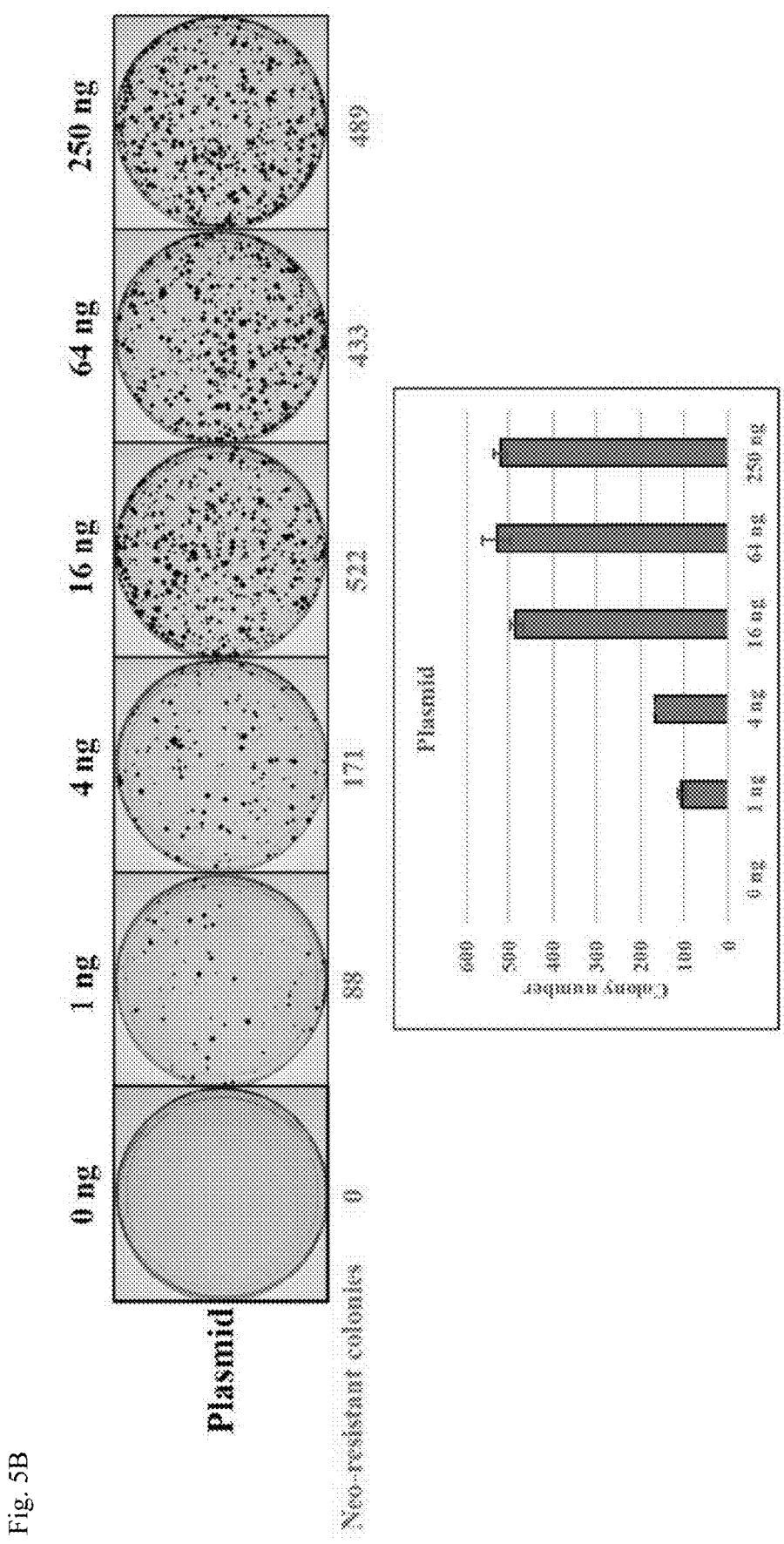
Figure 5C:
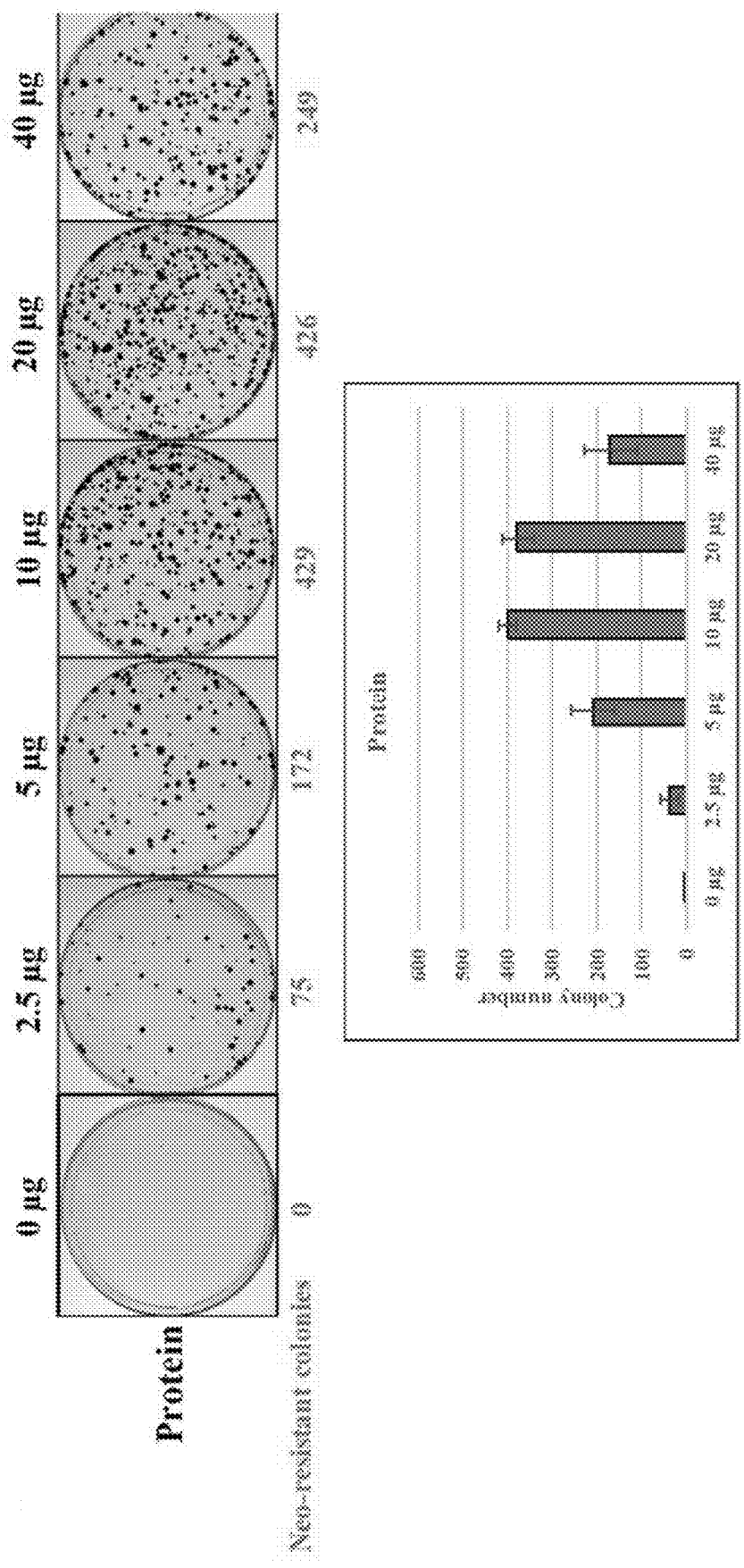

FIGS. 5(A) to 5(E) provide data demonstrating delivery of hsSB either as recombinant protein or encoded in a plasmid. FIGS. (A): retention of hsSB delivered into HeLa cells as protein or expressed from plasmid DNA. FIGS. 5(B) and 5(C): Representative transposition assays in HeLa cells demonstrate comparable transgene (neomycin resistance) insertion rate when using the hsSB transposase delivered as a plasmid (B) or as a protein (C). Error bars indicate the standard error of the mean from 2 independent experiments (n=2); FIG. 5(D) and FIG. 5(E): representative flow cytometric analysis by fluorescence activated cell sorting (FACS) of HeLa cells transfected with Venus-carrying transposon plasmid and: either an hsSB encoding plasmid, or hsSB protein, delivered by electroporation. Cells that acquired the transposon plasmid were sorted two days post-transfection; transposition efficiency was quantified 21 days later by FACS analysis.

Figure 6:
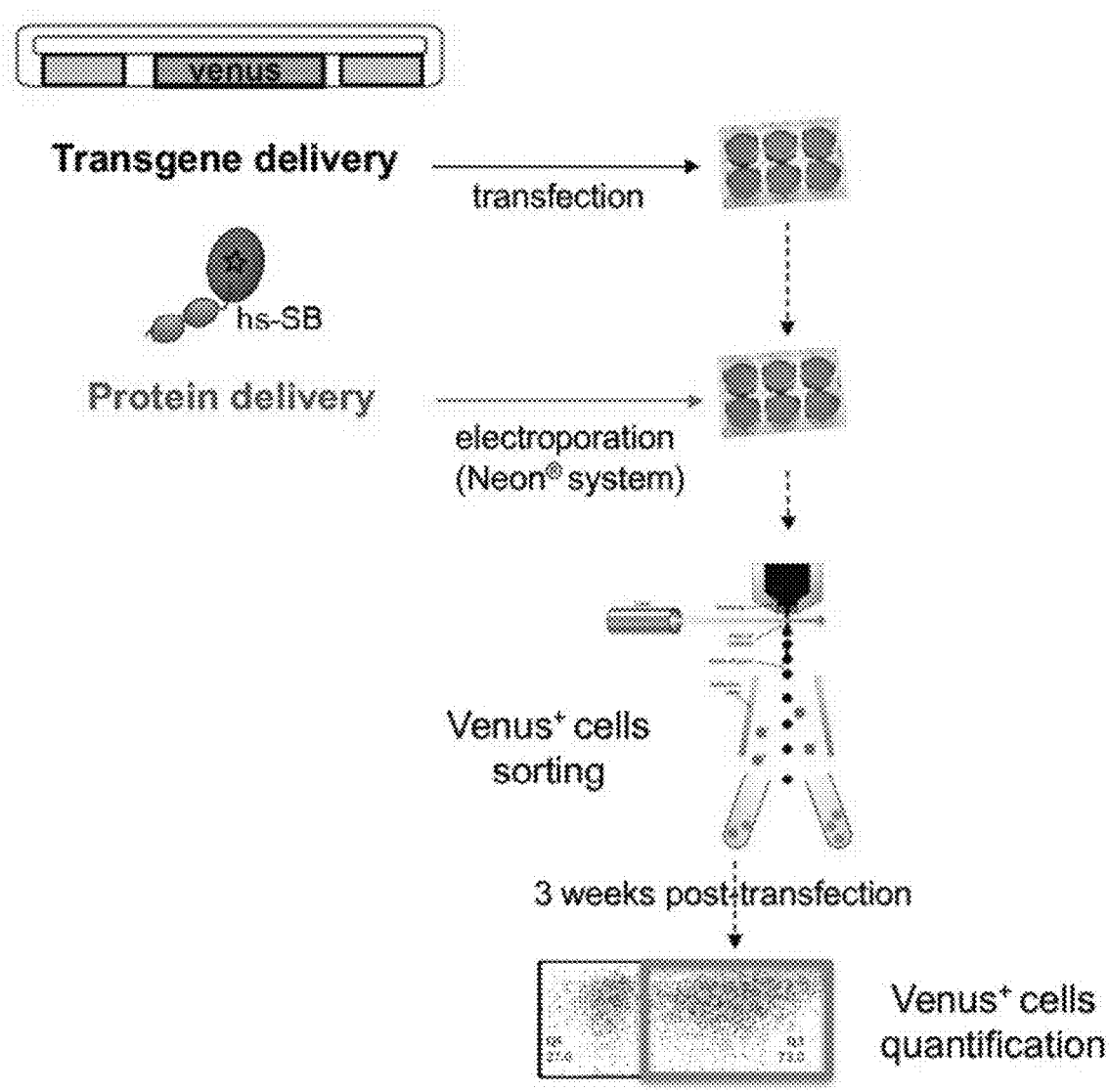

FIG. 6 is a schematic representation of the SBprotAct engineering procedure with quantification by cell sorting.

Figure 7:
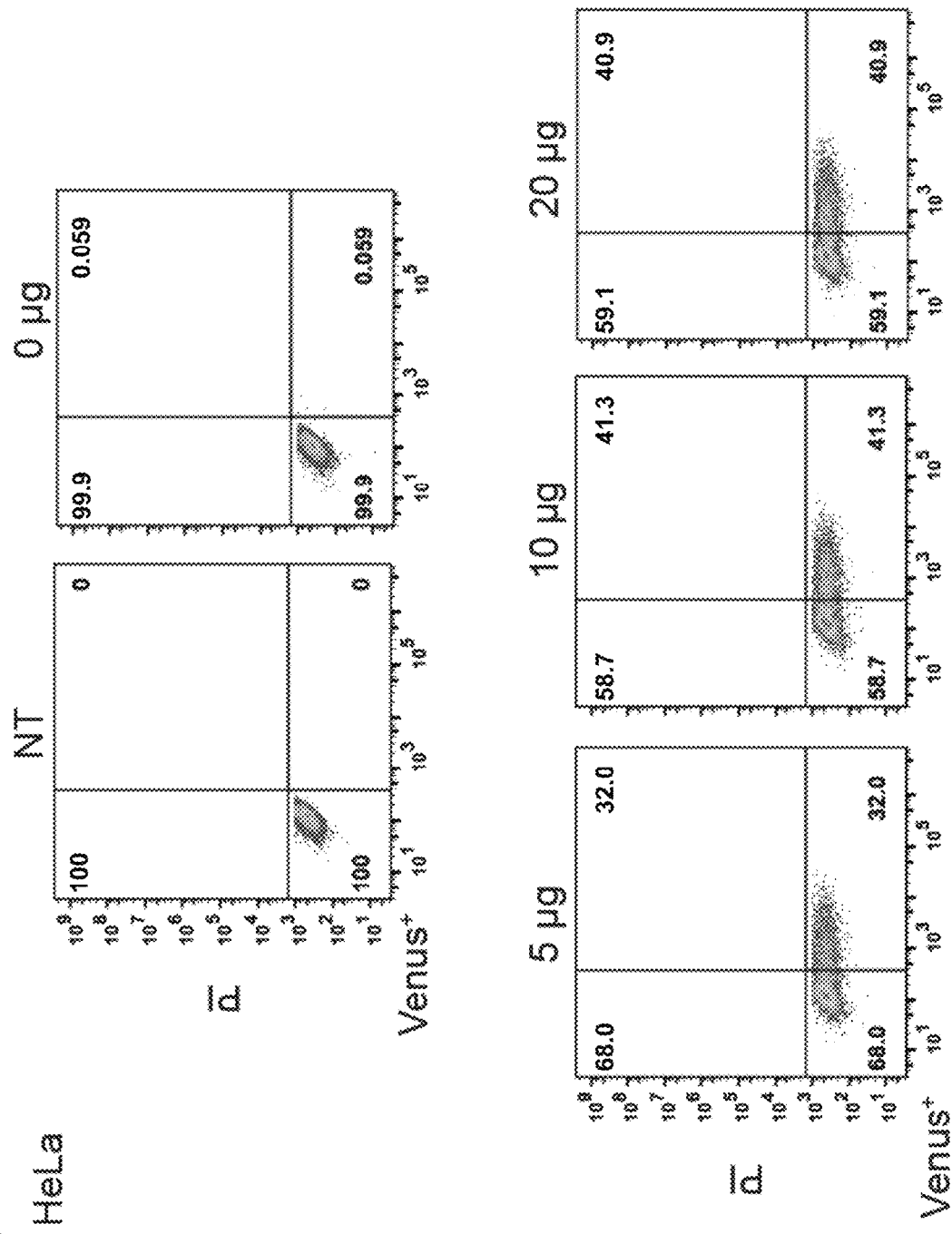

FIG. 7 shows results of representative flow cytometric analysis of HeLa cells transfected with Venus-carrying transposon plasmid and electroporated with hsSB transposase.

Figure 8:
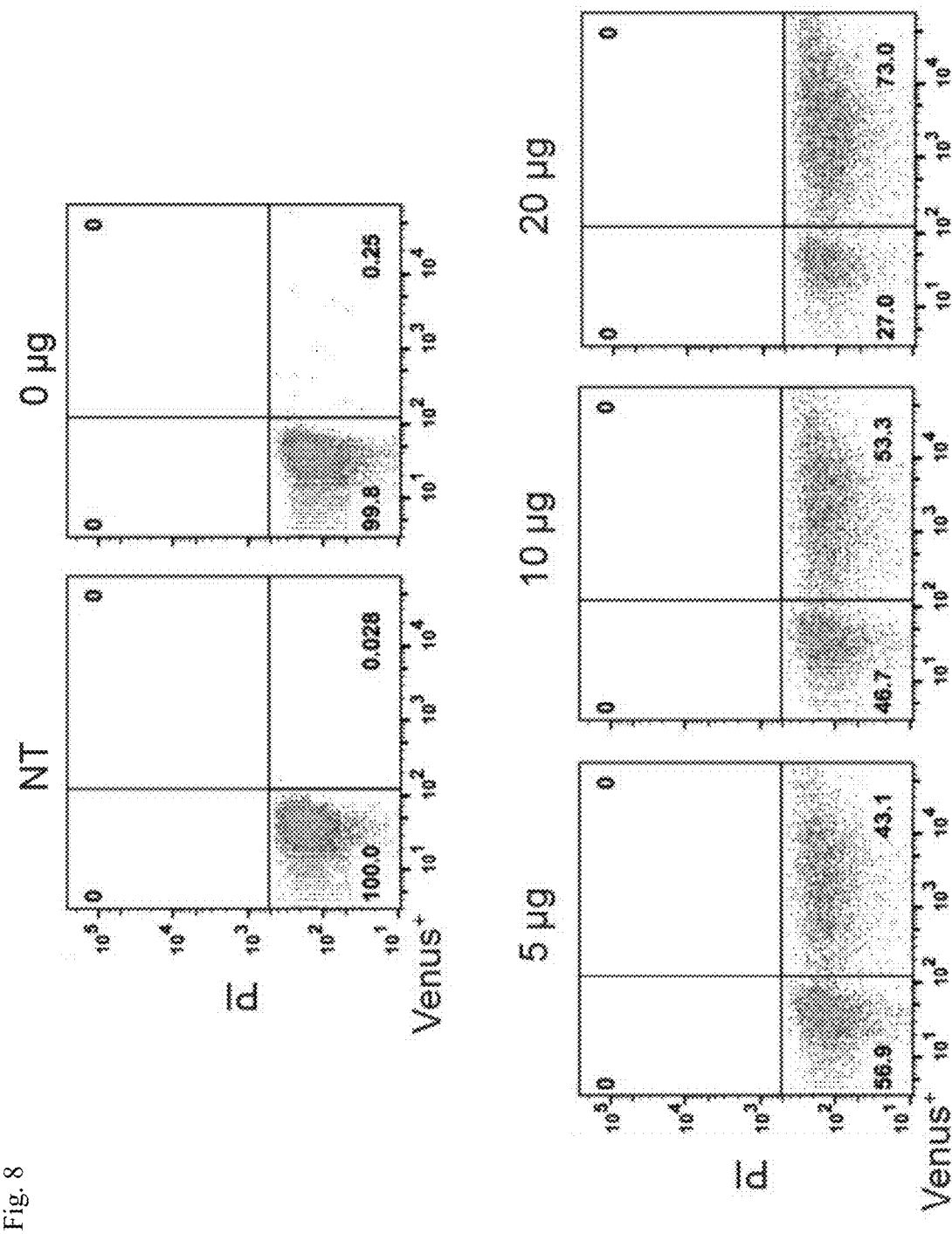

FIG. 8 shows results of representative flow cytometric analysis of Chinese Hamster Ovary (CHO) cells transfected with Venus-carrying transposon plasmid and electroporated with hsSB transposase.

Figure 9A:
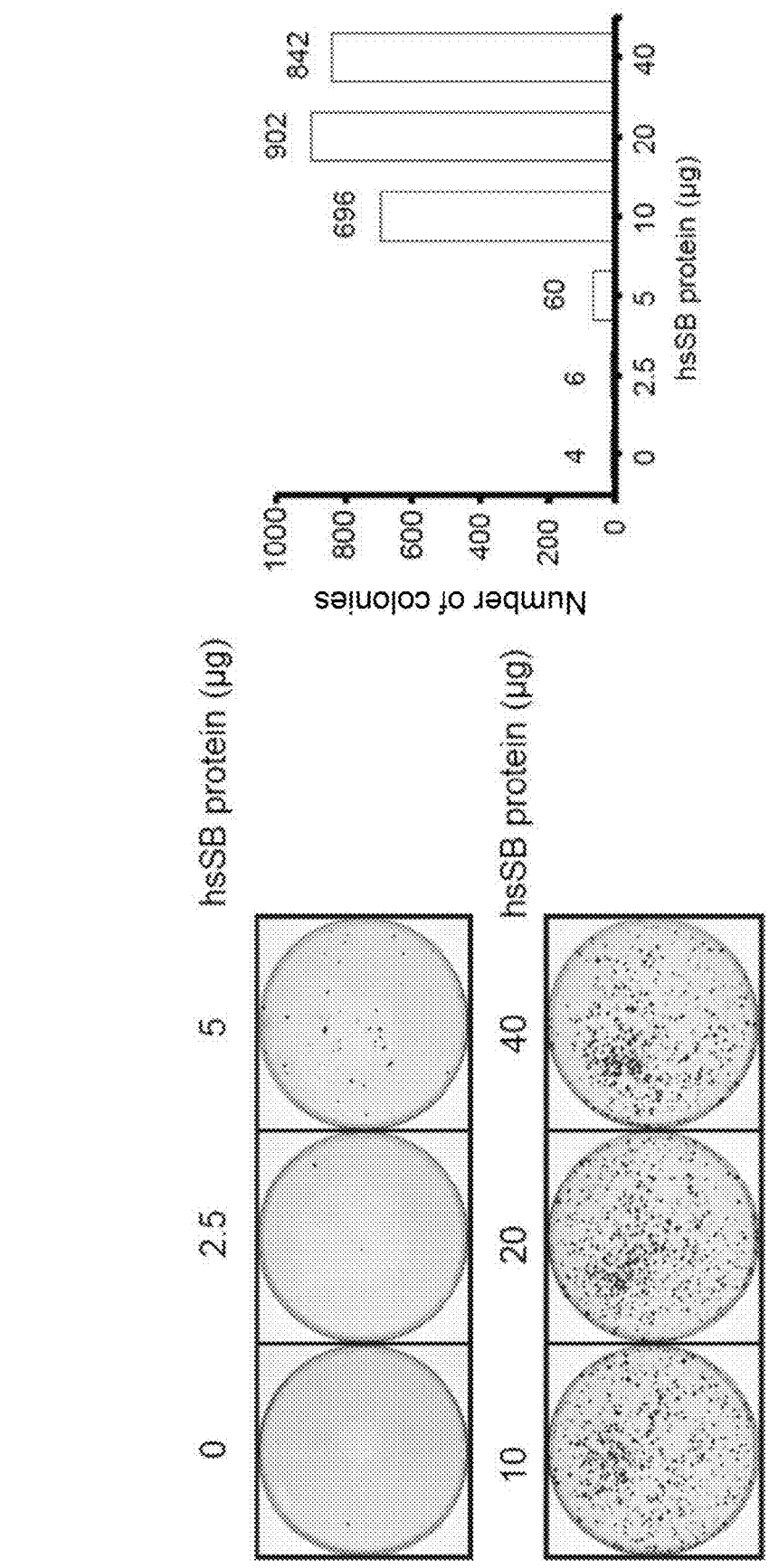

FIGS. 9(A), (B), and (C) show results from genetic engineering of mESCs by direct delivery of the hsSB transposase protein.

FIG. 10 is a table showing transgenesis efficiency of the SBprotAct system in different cell lines as quantified by flow cytometric analysis. Errors are indicated as standard deviation (n=2).

DETAILED DESCRIPTION

Prior Art Embodiments of Sleeping Beauty (SB) Transposase

Using SB for gene transfer is essentially a binary system, comprising the SB transposase in combination with a transposon that includes the gene intended for transfer into the target cell. Use of the non-viral SB vector in vivo reduces the risks of undesired immune response activation in patients, which constitutes a major safety concern connected to the use of viral vectors in gene therapy applications in general and in cancer immunotherapy (e.g. CAR-T cell therapy) in particular.

In contrast to gamma-retroviral and lentiviral vectors that preferentially insert into actively transcribed or regulatory regions, SB presents a close-to-random genomic integration pattern reducing the risk of insertional mutagenesis and genotoxicity. Differently from genome editing nucleases as zinc-finger, TALENs, and Cas9, the SB transposase directly and precisely integrates its cargo into the chromosome without generating potentially harmful double-strand breaks at the target locus. SB's insertion rates and safety do not depend on the efficiency of the repair machinery in the target cells. These advantages make SB the only non-viral gene delivery vehicle used for CAR-T cell engineering in clinical trials, which has triggered considerable commercial interest in the SB system in the last few years.

Although the SB system typically has lower gene-transfer efficiency than viral vectors, novel strategies—such as improved design and delivery methods for its components, as well as selective propagation of CAR positive cells—have recently increased the success of SB-mediated T cell engineering to levels similar to viral approaches.

Despite these improvements, important issues remain. In particular, long-term transposase expression can result in uncontrolled ongoing transposition, potentially leading to transgene remobilization, undesired insertion events, genome instability and cytotoxicity. Insertion of the SB transposase gene from the expression vector (e.g. by homologous recombination) may result in infinite transposase production and unintended acquisition of the transposase promoter might cause activation of oncogenes or disrupt gene regulatory networks in the target cells. This poses concerns regarding the safety of the current SB system and highlights the need for technological advances to reduce or alleviate these risks.

Improvements in the SB Transposase System Provided in this Disclosure

This disclosure circumvents limitations of the prior art transposase by providing an SB transposase adapted for delivery into the target cell in protein form. This achieves a tighter control of transfection efficiency and temporal control to improve safety of transposon-based cell engineering, especially for therapeutic applications.

This approach has not previously been possible, because of the difficulty in producing sufficiently quantity and quality of active SB transposase protein. This limitation was solved in this disclosure by adapting the amino acid sequence of the transposase to increase solubility. There is at least one mutated amino acid residue compared to a reference amino acid sequence-such as a non-mutated but artificial transposase or a wild-type enzyme—of the transposase, wherein the at least one mutated amino acid residue is located within the catalytic domain of the transposase. The catalytic domain is preferably within an amino acid sequence between residues 150 and 250 of for example SB100X (SEQ ID NO: 2). Reference transposases according to the invention are preferably SB transposases either as wild-type enzymes or genetically engineered enzymes such as SB10, SB11 or SB100X.

The transposase polypeptide has several surprising advantages compared to the prior art SBioox enzyme. Subsequent information in this disclosure that the transposase of the invention (1) has a higher protein yield in recombinant protein expression, (2) has increased solubility, which is advantageous for delivery of the protein via electroporation (better soluble in the electroporation buffer), (3) the enzyme is more stable and less prone to protein degradation and in particular more thermostable than the prior art enzyme which also is advantageous during electroporation.

This disclosure provides a safe and effective strategy to achieve efficient, stable and controlled genetic engineering of mammalian cells via the direct delivery of a mutated transposase variant. The new transposase variants of the invention are suitable for large-scale recombinant protein production and transfection, which allows for successful engineering of a range of mammalian cell lines and the manufacture of Chimeric Antigen Receptor (CAR) T-cells. The procedure for transgene integration using hsSB in protein form (named "SBprotAct") provides a novel approach that alleviates safety issues and enables maximal control of the transposase system in clinical applications. A transposase of the invention proved to create less insertions per cell at the same transgenesis rate and hence allows for a tightly controlled gene delivery.

Rational Mutagenesis of the SB100X Transposase to Obtain a Transposase that is More Soluble in Protein Form In FIG. 1(A), the left side shows the crystal structure of the SB100X transposase (hereinafter referred to as SB) catalytic domain is shown. Residues mutated to serines for the generation of the hsSB variant are shown as sticks. Right: Amino acid sequence of the full length hsSB transposase variant used for recombinant protein production. Bold underlined characters indicate serines substituting C176 and 1212 respectively in the SB100X sequence to obtain hsSB. Residues have also been introduced at the N-terminus for recombinant protein production.

FIG. 1(B) shows the recombinant production of hsSB protein of the invention. SDS-PAGE analysis of purified hsSB protein variant is provided. hsSB is recombinantly produced in *E. coli* (fused to N-terminal purification and solubility tags) in high quantity. hsSB is highly pure after tag removal and size exclusion chromatography (SEC). Purification yields of hsSB are shown in FIG. 1(C). Size exclusion chromatogram showing that hsSB is recombinantly produced at significantly higher yields (roughly double amounts) compared to SB, indicating improved solubility of the hsSB variant.

High solubility of hsSB in electroporation buffer is shown in FIG. 1(D). hsSB can be concentrated up to 50 fold (corresponding to 20 mg/mL), whereas SB undergoes precipitation at concentrations higher than 7 mg/mL. hsSB is highly soluble in the low salt buffer (used for electroporation), even at high protein concentration. While some precipitation is observed upon concentration, the vast majority of hsSB stays in the soluble fraction. SDS-PAGE analysis of purified SB proteins upon incubation at 37° C. is shown in FIG. 1(E). SB exhibits degradation (degradation products indicated by asterisks) even upon short incubation at physiological temperature, while hsSB does not. As shown in FIG. 1(F), hsSB is more thermostable than SB. CD measurements of both proteins in close to physiological (200 mM NaCl, pH 7.5) buffer condition.

hsSB has the same fold as SB, as shown by the data in the left panel of FIG. 1(F). Nonetheless, hsSB is significantly more thermostable; it does not completely unfold at 95° C. (right panel). Considering that electroporation heats the sample, this property is highly advantageous for protein transfection. Upon long-term storage hsSB is better preserved than SB (FIG. 1(G)). Left panel: SDS-PAGE analysis of purified SB proteins upon long-term storage at −80° C., showing that SB undergoes significant degradation after freezing, while hsSB does not. Right panel: Mass spectrometry analysis of the bands indicated by boxes and asterisks on the left confirms that the bands correspond to degradation products of the SB protein.

Use of the hsSB Transposase Protein for Gene Delivery into HeLa Cells

A strategy for gene delivery is depicted in FIG. 2. Transgene (neomycin resistance gene) insertions are driven by transposition activity of the transfected hsSB transposase (FIG. 3). Top: Representative transposition assay in HeLa cells. Number of neomycin resistant colonies is shown in parenthesis. Bottom: Quantification of the transposition assay in HeLa cells. Error bars represent standard error (n=3).

FIG. 4 shows insertion sites as derived by sequence analysis of the neomycin locus from isolated neomycin positive HeLa cells. Insertions of SB IRs correctly occur at TA dinucleotides. FIG. 5(A) shows the retention of hsSB delivered into HeLa cells as protein or expressed from plasmid DNA. Western blot analysis shows almost complete loss of delivered hsSB protein 48 hours after electroporation, whereas cells transfected with hsSB expression plasmids produce high level of protein continuously from 24 hours to 5 days after transfection. Western blot was performed on lysate from HeLa cells transfected with 0.5 μg of pSBTer (Tpn) and electroporated with 10 μg hsSB protein or transfected with 0.5 μg hsSB expression plasmid. Samples were taken at the indicated time points and 20 μg of the total lysate were separated by electrophoresis and transferred to a nitrocellulose membrane. The SB was detected with anti-SB antibody. The internal loading control was glyceraldehyde 3-phosphate dehydrogenase (GAPDH) detected with anti-GAPDH antibody. Measurement of the intensities of the bands allows to quantify hsSB persistence in HeLa cells over time (as shown in the chart on the left).

A comparison of genetic engineering efficiency in HeLa cells as executed by hsSB provided on an expression plasmid or directly delivered as a protein by electroporation is shown in FIG. 5(B) to 5 (E). As can be seen, genetic engineering efficiency does not depend on the transfection method, although protein electroporation is for a shorter time period more efficient, whereas plasmid transfection yields long term expression of the transposase.

A schematic representation of the SBprotAct engineering procedure with quantification by cell sorting is shown in FIG. 6. FIG. 7 shows a representative flow cytometric analysis of HeLa cells transfected with Venus-carrying transposon plasmid and electroporated with hsSB transposase. Venus-positive cells are identified 3 weeks post-transfection, so as to select for transposition positive cells. The electroporated hsSB protein amounts are indicated above each chart. Y axis: propidium iodide (PI) staining to select living cells. X-axis: green fluorescence from Venus. NT: non-transfected.

Use of the Transposase Protein for Gene Delivery into CHO Cells and Mouse Embryonic Stem Cells (mESCs)

A representative flow cytometric analysis of Chinese Hamster Ovary (CHO) cells transfected with Venus-carrying transposon plasmid and electroporated with hsSB transposase is shown in FIG. 8. Venus-positive cells are identified 3 weeks post-transfection, so as to select for transposition positive cells. The electroporated hsSB protein amounts are indicated above each chart. Y axis: propidium iodide (PI) staining to select living cells. X-axis: green fluorescence from Venus. NT: non-transfected.

Figure 9B:
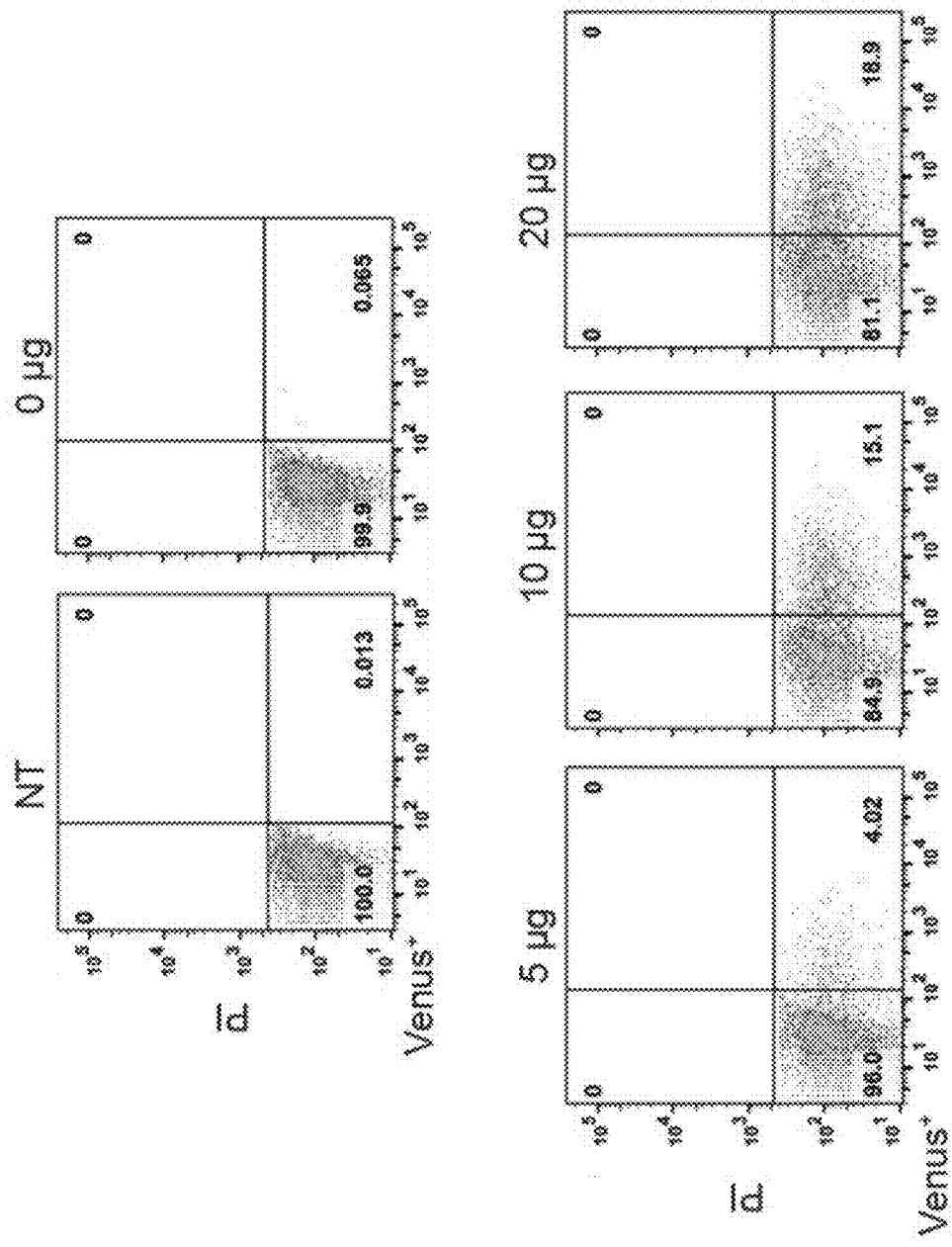
Figure 9C:
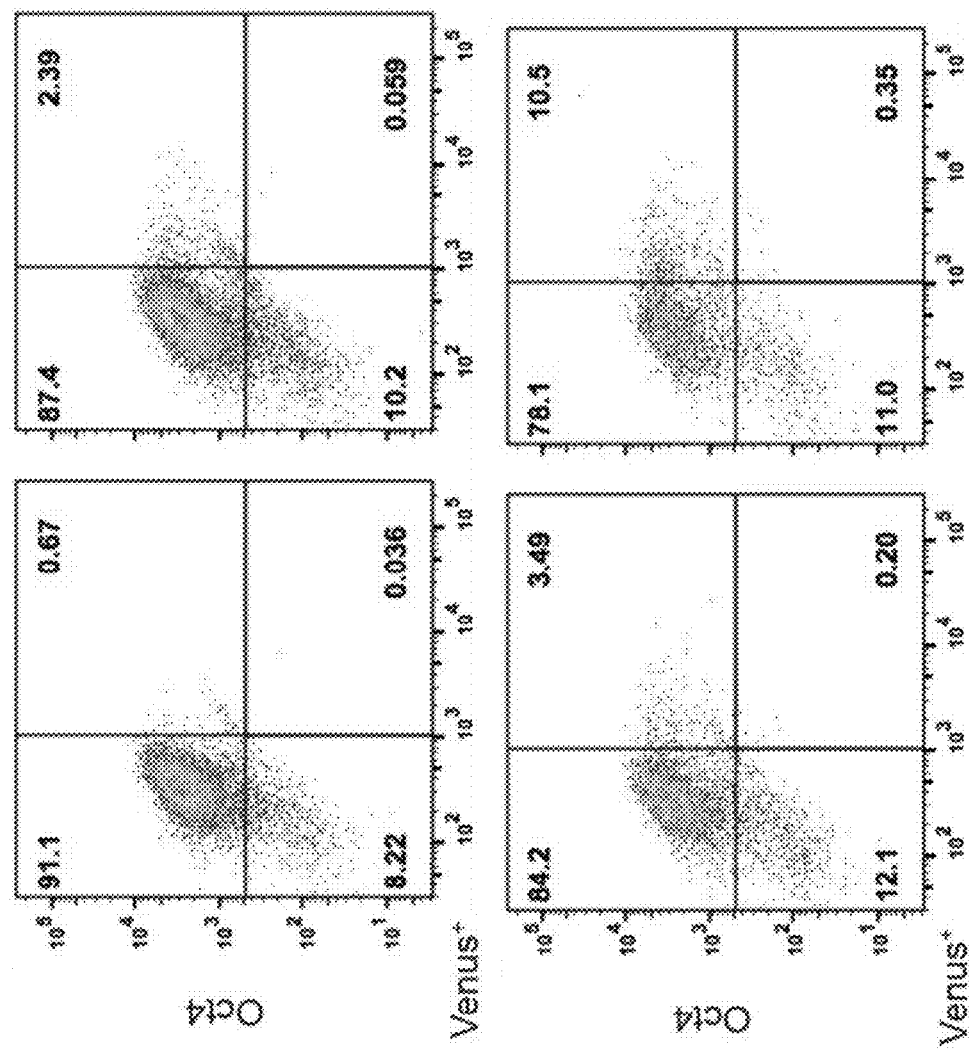

FIGS. 9(A) to 9 (C) shows genetic engineering of mESCs by direct delivery of the hsSB transposase protein. FIG. 9(A): Representative transposition assay in mouse embryonic stem cells (mESCs) demonstrating efficient transgene (neomycin resistance) insertions by the transfected hsSB transposase. FIG. 9(B): Representative flow cytometric analysis of mESCs transfected with Venus-carrying transposon plasmid and electroporated with hsSB transposase. Venus-positive cells are identified 3 weeks post-transfection, so as to select for transposition positive cells. The electroporated hsSB protein amounts are indicated above each chart. Y axis: propidium iodide (PI) staining to select living cells. X-axis: green fluorescence from Venus. NT: nontransfected. FIG. 9(C): Oct4 staining confirms that engineered mESCs retain their pluripotent state FIG. 10 shows transgenesis efficiency of the SBprotAct system in different cell lines as quantified by flow cytometric analysis. Errors are indicated as standard deviation (n=2).

A representative transposition assay was used in an experiment in mouse embryonic stem cells (mESCs), demonstrating efficient transgene (neomycin) insertions by the transfected hsSB transposase. Flow cytometric analysis was done on mESCs transfected with Venus carrying transposon plasmid and electroporated with hsSB transposase. Venus-positive cells were identified 3 weeks post-transfection, so as to select for transposition positive cells. Oct4 staining confirmed that engineered mESCs retain their pluripotent state.

Benefits of this Technology

The novel transposase variant and transfection strategy (SBprotAct) establishes a new generation of the SB transposon system for cell engineering based on the use of purified transposase protein, which is unprecedented in itself to date. In standard SB-based applications, expression of the SB transposase is achieved either from an expression plasmid or from protein-encoding messenger RNA delivered into target cells. In ongoing clinical gene therapy trials, expression plasmids are exclusively used as sources of the SB transposase.

In comparison to transposase gene delivery, direct hsSB protein delivery in SBprotAct provides:
a) Comparable transgenesis rates in diverse cell types.
b) No risks of transposase-gene or -promoter integration, circumventing uncontrolled long-term transposition and undesired transcriptional activation (of e.g. oncogenes) in the target cells.
c) No need for transcription and translation in the target cells. This expands the applicability of SB-mediated engineering to cells in which protein over-expression is difficult and/or compromises cell viability.
d) Fast cell engineering and rapid protein turnover, as hsSB protein is degraded within 48 h from delivery. Therefore hsSB protein acts in a hit-and-run fashion, minimizing off-target activities (see below).
e) Lower cytotoxicity, reduced risks of insertional mutagenesis and transgene remobilization due to limited temporal window of transposition.
f) Lower number of insertions per cell at the same transgenesis rate, minimizing genome perturbations.
g) Dose-dependent efficiency. By varying the concentration of the transfected hsSB protein, the number of positive clones can be tightly controlled.
h) Discrete and adjustable number of insertion events. hsSB-mediated engineering produces clones with discrete number of insertions per genome, which can be adjusted by varying the protein dose. In contrast, uncontrolled level and time of transposition from expression plasmids leads to heterogeneous, multicopy clones.

Figures 1H, 1I:
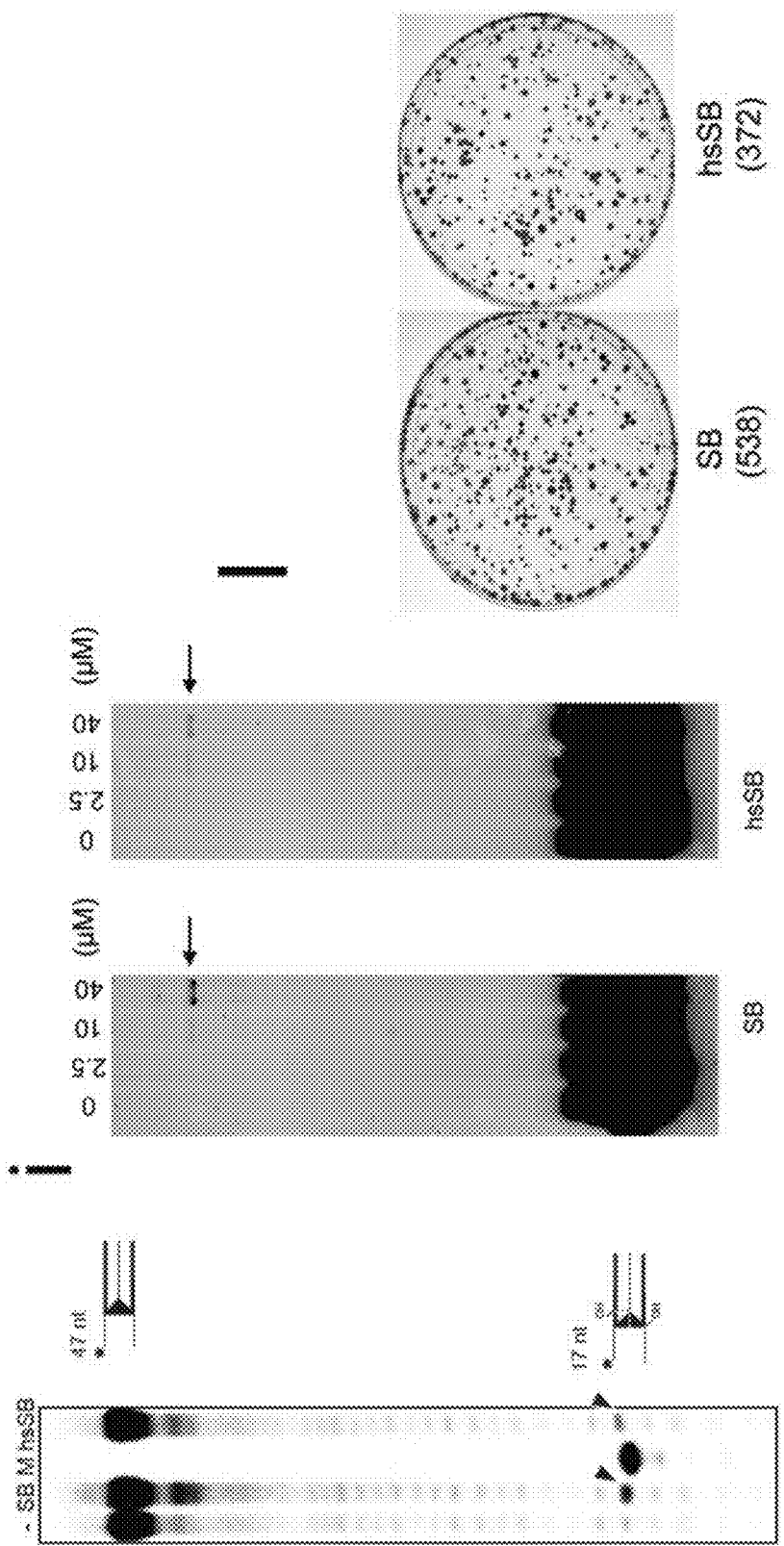

For CAR-T cell generation, the use of mRNA has been explored as alternative source of SB transposase, but the instability of mRNA raises quality control issues that could hinder widespread use for therapy. hsSB protein delivery offers several advantages in comparison to mRNA delivery:
i) Independence from cellular translation efficiency and regulation.
j) Even tighter and more direct control of transposition efficiency, since the SB transposase immediately works after transfection without the need for translation.
k) The possibility to assess protein quality and activity in vitro prior to application (assays described in publication and shown in FIG. 1(H). This is of particular relevance for quality control procedures in a commercial or clinical setting.

Before the technology provided in this disclosure, highly-efficient mammalian cell engineering has been achieved only for the PiggyBac transposase, but required incorporation of the protein into lentiviral particles. SBprotAct described here provides for the first time a completely virus-free system for efficient delivery of a transposase protein in a medically relevant setting, avoiding all safety concerns and financial limitations connected to the use and the manufacture of viral vectors.

The SBprotAct system of this disclosure opens up new possibilities to achieve maximal control of SB transposition in its genetic engineering applications, making SB an ever-safer genetic tool. Direct delivery of the hsSB protein allows rapid transposase clearance from the cell, avoiding the undesired effects of long-term transposition. By using the transposase in protein form, the rates and time frame of active transgene insertion can be finely modulated and do not depend on the timeline and stochastic events in transposase expression (from plasmids) or translation (from mRNAs) by the cellular machinery, thereby also avoiding the fitness costs for the target cell.

SB is the only non-viral gene delivery tool currently used to manufacture CAR T-cells in clinical trials and it has already advanced quite far in clinical development. While preserving all advantages of the current SB system, including simplicity, ease and low cost, the SBprotAct of the invention provides a novel approach to overcome safety issues concerning the use of the current SB system in clinical applications.

Exemplary Transposase Variants

The term "transposase" as used herein refers to an enzyme that is a component of a functional nucleic acid-protein complex capable of transposition and which is mediating transposition. The term "transposase" also refers to integrases from retrotransposons or of retroviral origin. A "transposition reaction" as used herein refers to a reaction where a transposon inserts into a target nucleic acid. Primary components in a transposition reaction are a transposon and a transposase or an integrase enzyme. For example, the transposase system according to the invention is preferably a so called "Sleeping Beauty (SB)" transposase. In certain aspects, the transposase is an engineered enzyme with improved characteristics such as increased enzymatic function. Some specific examples of an engineered SB transposases include, without limitation, SBio, SBn or SBioox SB transposase (see, e.g., Mates et al., Nat. Gen. 2009, incorporated herein by reference). Other transposition systems can be used, e.g., Tyi (Devine and Boeke, 1994, and WO 95/23875), Tn7 (Craig, 1996), Tn 10 and IS 10 (Kleckner et al. 1996), Mariner transposase (Lampe et al., 1996), Tel (Vos et al., 1996), Tn5 (Park et al., 1992), P element (Kaufman and Rio, 1992) and Tn3 (Ichikawa and Ohtsubo, 1990), bacterial insertion sequences (Ohtsubo and Sekine, 1996), retroviruses (Varmus and Brown 1989), and retrotransposon of yeast (Boeke, 1989).

The reference transposase is a Sleeping Beauty (SB) transposase, and preferably is SB100X (SEQ ID NO: 2) or an enzyme derived from SB100X. A transposase polypeptide according to the invention is a polypeptide having transposase activity, wherein the at least one mutated amino acid residue is a residue that is located between amino acid 150 and 250 of SB transposase, preferably SB100X transposase.

There may be at least two mutated amino acid residues, or at least three, four, five or more amino acids. It is preferably that the transposase polypeptide of the invention when its sequence is aligned with the sequence of an SB transposase, preferably SB100X, is mutated in any one of amino acids 170 to 180 and/or 207 to 217. More preferably the at least one mutated amino acid residue is selected from amino acid 176 and/or 212 of SB transposase, preferably of SB100X. Most preferably the at least one mutated amino acid residue is mutated into a serine residue, and preferably is C176S, or C176S and I212S.

The transposase polypeptide of the invention may have an amino acid sequence having at least 60%, 70%, 80%, 90%, 95%, 96%, 97%, 98%, 99%, most preferably 100% sequence identity to the amino acid sequence between residues 150 to 250 as shown in SEQ ID NO: 1 (hsSB). It is preferred that the transposase polypeptide includes at least a C176 mutation, preferably C176S, compared to the sequence in SEQ ID NO: 2. Even more preferably the transposase polypeptide further includes the mutation at position I212, preferably I212S.

In some embodiments the transposase polypeptide of the invention comprises an amino acid sequence having at least 60%, 70%, 80%, 90%, 95%, 96%, 97%, 98%, 99%, most preferably 100% sequence identity to the full length amino acid sequence as shown in SEQ ID NO: 1 or 3 (hsSB). Preferably, although the degree of sequence identity is in some embodiments below 100%, the above indicated at least one mutation shall be present in the transposase polypeptide of the invention.

As used herein, the terms "identical" or percent "identity", when used anywhere herein in the context of two or more nucleic acid or protein/polypeptide sequences, refer to two or more sequences or subsequences that are the same or have (or have at least) a specified percentage of amino acid residues or nucleotides that are the same (e.g., at, or at least, about 60% identity, preferably at, or at least, 65%, 70%, 75%, 80%, 85%, 90%, 91%, 92%, 93% or 94%, identity, and more preferably at, or at least, about 95%, 96%, 97%, 98%, 99%, or higher identity over a specified region-preferably over their full length sequences-, when compared and aligned for maximum correspondence over the comparison window or designated region) as measured using a sequence comparison algorithms, or by manual alignment and visual inspection (see, e.g., NCBI web site). In a particular embodiment, for example when comparing the protein or nucleic acid sequence of the transposase of the invention to for example a reference (non-mutated transposase), the percentage identity can be determined by the Blast searches provided in NCBI; in particular for amino acid identity, those using BLASTP 2.2.28+ with the following parameters: Matrix: BLOSUM62; Gap Penalties: Existence: 11, Extension: 1; Neighboring words threshold: 11; Window for multiple hits: 40.

The transposase polypeptide of the invention has an increased solubility compared to a reference non-mutated transposase polypeptide, preferably wherein the reference non-mutated transposase polypeptide is SB100X transposase, preferably as shown in SEQ ID NO: 2 (non-mutated SB100X).

Another aspect of the invention is a polynucleotide comprising a nucleic acid sequence encoding for a transposase polypeptide as described herein above, preferably wherein the polynucleotide is RNA or DNA. For example RNA may be provided in the form of messenger RNA (mRNA) that allows for a direct translation into the transposase polypeptide of the invention if the mRNA is introduced into a biological cell.

Another aspect of the invention is a vector comprising a polynucleotide of the invention. Also provided is an expression construct, comprising an expressible polynucleotide encoding a transposase polypeptide of the invention and a promoter element, wherein the promoter element is operably linked to the expressible polynucleotide to allow for the expression of the polynucleotide.

Also provided is a recombinant cell, comprising a transposase polypeptide of the invention, a polynucleotide of the invention, or a vector and/or an expression construct of the invention. The recombinant cell is preferably a cell suitable for recombinant protein expression, preferably for recombinant protein expression of the transposase polypeptide of the invention. Such as a bacterial cell or eukaryotic cell, most preferably a bacterial cell such as *E. coli* or an insect cell, such as *Drosophila* S2 cell or a mammalian cell such as HEK293T cell.

Yet another aspect relates to a transposon system comprising
(a) a transposon unit containing inverted terminal repeats (ITRs) or direct terminal repeats (DTRs) that flank a sequence of interest to be inserted into the genome of a target cell; and
(b) a transposase polypeptide, a polynucleotide, a vector and/or an expression construct as described herein above.

The term "transposon unit" refers to the nucleic acid construct that constitutes the transposon genetic sequence with the target sequence that is to be introduced into a target cell genome. Usually a transposon unit will be nucleic acid and may be a vector of any form suitable for transposition.

The term "inverted terminal repeat" refers to a sequence located at one end of a transposon unit that can be cleaved by a transposase polypeptide when used in combination with a complementary sequence that is located at the opposing end of the vector or transposon unit. The pair of inverted terminal repeats is involved in the transposition activity of the transposon of the transposon unit of the present disclosure, in particular involved in DNA addition or removal and excision and integration of DNA of interest. In one example, at least one pair of an inverted terminal repeat appears to be the minimum sequence required for transposition activity in a plasmid. In another example, the transposon unit of the present disclosure may comprise at least two, three or four pairs of inverted terminal repeats. As would be understood by the person skilled in the art, to facilitate ease of cloning, the necessary terminal sequence may be as short as possible and thus contain as little inverted repeats as possible. Thus, in one example, the transposon unit of the present disclosure may comprise not more than one, not more than two, not more than three or not more than four pairs of inverted terminal repeats. In one example, the transposon unit of the present disclosure may comprise only one inverted terminal repeat. Whilst not wishing to be bound by theory, it is envisaged that having more than one inverted terminal repeat may be disadvantageous as it may lead to non-specific transposase binding to the multiple inverted terminal repeats and resulting in the removal of desired sequence or insertion of undesirable sequences. The inverted terminal repeat of the present disclosure may form either a perfect inverted terminal repeat (or interchangeably referred to as "perfect inverted repeat") or imperfect inverted terminal repeat (or interchangeably referred to as "imperfect inverted repeat"). As used herein, the term "perfect inverted repeat" refers to two identical DNA sequences placed at opposite direction. The above descriptions for transposon units with ITR also apply for transposon units with DTRs.

A transposon system that could be used with the inventive transposon polypeptide/nucleic acid of the invention is for example disclosed in WO 2017/050448 A1, which is included in the present disclosure by reference. A transposon system according to the invention is preferable, wherein said transposon unit of (a) is in the form of a minicircle. However, the transposon unit may be other nucleic acid systems. However, minicircles are preferable in the context of T cell engineering.

Another aspect of the invention then pertains to the use of a transposon system as described for gene delivery into a target cell. The gene delivery is preferably an ex vivo gene delivery into a target cell, such as a target cell selected from a stem cell, such as a hematopoietic or embryonic stem cell, T-cell, B-cell or Chinese hamster ovary (CHO) cell. Most preferably is the system or the compounds of the invention used in the generation of CAR T-cells.

The term "chimeric antigen receptor" (CAR) refers to an extracellular antigen-binding domain that is fused to an intracellular signaling domain of a cell, such as a T cell or a NK-92 cell.

Further provided is a method for gene delivery into a target cell comprising the following steps:
 (a) bringing into contact the transposon system as described with a target cell;
 (b) culturing said target cell under conditions permissive to the culture of said target cell.

In another aspect, a pharmaceutical composition is provided, comprising a transposase polypeptide, a polynucleotide, a vector, and/or an expression construct, together with a pharmaceutically acceptable carrier and/or excipient.

Another aspect then pertains to a kit comprising:
 (a) a transposon unit containing inverted terminal repeats (ITRs) or DTRs that flank a sequence of interest to be inserted into the genome of a target cell; and
 (b) a transposase polypeptide, a polynucleotide, a vector, and/or an expression construct of the invention as described herein.

The compounds and systems of the invention may preferably find application in medicine. Therefore, such compounds and systems of the invention are preferably for use in the treatment of a disease. Such diseases may be proliferative disease, such as cancer. For a cancer treatment, the invention may be used in context of the generation of modified immune cells. For example, the invention can be used to introduce into immune cells T cell receptors (TCR) or CARs or other immune molecules, to strengthen and target a patient's immune system against cancer cells. Immune cells that can be modified may be selected from human T lymphocytes or B cells. Other diseases that could benefit from the invention are genetic disorders that are characterized by the loss of a gene function. In such diseases cells could be modified with the invention to include a healthy copy of the disease associated gene. Other target cells that are preferably used in context with the invention are stem cells such as, for example, embryonic, or adult stem cells, such as hematopoietic stem cells.

The figures, sequences, and examples in this disclosure merely serve to illustrate the invention and should not be construed to restrict the scope of the invention to the particular embodiments of the invention described in the examples. All references as cited herein are hereby incorporated in their entirety by reference.

Transposase Protein Sequences (hsSB)
SEQ ID NO: 1
MGKSKEISQDLRKRIVDLHKSGSSLGAISKRLAVPRSSVQTIVRKYKHHG

TTQPSYRSGRRRVLSPRDERTLVRKVQINPRTTAKDLVKMLEETGTKVSI

STVKRVLYRHNLKGHSARKKPLLQNRHKKARLRFATAHGDKDRTFWRNVL

WSDETKIELFGHNDHRYVWRKKGEA-S-KPKNTIPTVKHGGGSIMLWGCF

AAGGTGALHKIDG-S-MDAVQYVDILKQHLKTSVRKLKLGRKWVFQHDND

PKHTSKVVAKWLKDNKVKVLEWPSQSPDLNPIENLWAELKKRVRARRPTN

LTQLHQLCQEEWAKIHPNYCGKLVEGYPKRLTQVKQFKGNATKY (non mutated SB100X)
SEQ ID NO: 2
MGKSKEISQDLRKRIVDLHKSGSSLGAISKRLAVPRSSVQTIVRKYKHHG

TTQPSYRSGRRRVLSPRDERTLVRKVQINPRTTAKDLVKMLEETGTKVSI

STVKRVLYRHNLKGHSARKKPLLQNRHKKARLRFATAHGDKDRTFWRNVL

WSDETKIELFGHNDHRYVWRKKGEA-C-KPKNTIPTVKHGGGSIMLWGCF

AAGGTGALHKIDG-I-MDAVQYVDILKQHLKTSVRKLKLGRKWVFQHDND

PKHTSKVVAKWLKDNKVKVLEWPSQSPDLNPIENLWAELKKRVRARRPTN

LTQLHQLCQEEWAKIHPNYCGKLVEGYPKRLTQVKQFKGNATKY (hsSB for recombinant expression)
SEQ ID NO: 3
GPM-MGKSKEISQDLRKRIVDLHKSGSSLGAISKRLAVPRSSVQTIVRKY

KHHGTTQPSYRSGRRRVLSPRDERTLVRKVQINPRTTAKDLVKMLEETGT

KVSISTVKRVLYRHNLKGHSARKKPLLQNRHKKARLRFATAHGDKDRTFW

RNVLWSDETKIELFGHNDHRYVWRKKGEA-S-KPKNTIPTVKHGGGSIML

WGCFAAGGTGALHKIDG-S-MDAVQYVDILKQHLKTSVRKLKLGRKWVFQ

HDNDPKHTSKVVAKWLKDNKVKVLEWPSQSPDLNPIENLWAELKKRVRAR

RPTNLTQLHQLCQEEWAKIHPNYCGKLVEGYPKRLTQVKQFKGNATKY

Underlined are mutated or to-be mutated residues. Bold and italic are residues introduced for recombinant protein expression.

---

The invention claimed is:

1. An improved method for inserting a transgene into the genome of a living host cell;
  wherein the method comprises introducing both a transposon that contains the transgene and a polynucleotide vector that encodes a Sleeping Beauty transposase into the host cell; and culturing the cell under conditions wherein the transposase is expressed in the cell and catalyzes insertion of the transgene into the cell's genome;
  wherein the improved method comprises the following:
  (a) identifying a variant transposase that has the following properties:
    (I) it is at least 90% identical to Sleeping Beauty transposase SB100X shown in SEQ ID NO: 2;
    (II) it differs from SB100X in that a plurality of amino acids in the catalytic domain of SB100X, which consists of amino acids 150 to 250 of SEQ ID NO: 2, have each been changed to an amino acid that does not appear at that position in SEQ ID NO: 2; and
    (III) as a consequence of the amino acids changed in (II), the variant transposase is demonstrably more soluble in electroporation buffer than SB100X;
  (b) obtaining the variant transposase as an isolated protein; and
  (c) introducing an effective amount of said protein into the host cell in place of said polynucleotide vector, thereby catalyzing insertion of the transgene into the cell's genome.

2. The method of claim 1, wherein the variant transposase is identified in step (a) by a process that comprises:
  (i) producing a plurality of variant transposase candidates, each of which is at least 90% identical to the amino acid sequence of Sleeping Beauty transposase SB100X and includes a plurality of amino acids between amino acids 150 and 250 of SEQ ID NO: 2 that have been changed from a non-polar to a polar amino acid;
  (ii) determining solubility of each of the candidates;
  (iii) introducing each of the candidates into a host cell along with a transposon containing a reporter gene; and
  (iv) determining insertion of the reporter gene into each of the host cells as an indication of transposase activity; thereby identifying at least one of the candidates as having at least 2-fold increased solubility in a low-salt electroporation buffer relative to SB100X while maintaining transposase activity.

3. The method of claim 2, wherein the candidates are designed by rational mutagenesis with reference to the crystal structure of SB100X.

4. The method of claim 2, wherein at least one amino acid between positions 170 to 180 of SEQ ID NO: 2 has been changed, and at least one amino acid between positions 207 to 217 of SEQ ID NO: 2 has been changed.

5. The method of claim 2, wherein the reporter gene is a drug resistance gene, and transposase activity is determined by counting colonies of cells that survive after culturing in a medium that contains the drug.

6. The method of claim 2, wherein the reporter gene encodes a fluorescent protein, and transposase activity is determined by fluorescence-activated cell sorting (FACS).

7. The method of claim 1, wherein the variant transposase is obtained as an isolated protein in step (b) by expressing a polynucleotide encoding the variant transposase; and purifying protein obtained therefrom.

8. The method of claim 1, wherein at least one of the amino acids that is changed in the variant transposase identified in step (a) replaces a non-polar amino acid in or around the DNA binding site of the crystal structure with a polar amino acid.

9. The method of claim 1, wherein at least one of the amino acids that is changed in the variant transposase identified in step (a) removes a cysteine from the surface of the crystal structure.

10. The method of claim 1, wherein the variant transposase is soluble in a low salt electroporation buffer at concentrations above 20*mg/mL.

11. The method of claim 1, wherein the variant transposase is more thermostable upon freezing and during storage at −80° C. compared with SB100X.

12. The method of claim 1, wherein the variant transposase has higher transposase activity than SB100X.

13. The method of claim 1, wherein the variant transposase when inserted into a host cell as an isolated protein has transposase activity that is comparable to transposase activity expressed in the host cell from a polynucleotide vector.

14. An improved method for inserting a transgene into the genome of a living host cell, comprising:
 (a) obtaining a variant transposase in protein form,
 wherein the variant transposase has been identified as having the following properties:
  (I) it is at last 90% identical to Sleeping Beauty transposase SB100X shown in SEQ ID NO: 2;
  (II) it differs from SB100X in that a plurality of amino acids in SEQ ID NO: 2 have each been changed to an amino acid that does not appear at that position of SEQ ID NO: 2;
  (III) as a consequence of the amino acids changed in (II), the mutated transposase is demonstrably more soluble in electroporation buffer than SB100X;
 wherein at least one of the amino acids that has been changed is between amino acids 170 to 180 of SEQ ID NO: 2, and at least one of the amino acids that has been changed is between amino acids 207 to 217 of SEQ ID NO: 2;
 (b) introducing an effective amount of the variant transposase into the host cell in protein form in combination with a transposon that contains the transgene; and
 (c) culturing the cell under conditions wherein said protein catalyzes insertion of the transgene into the genome of the host cell.

15. The method of claim 14,
 wherein at least two of the amino acids that have been changed are changed from a non-polar to a polar amino acid.

16. The method of claim 14, wherein at least one of the amino acids that has been changed is at position 176 of SEQ ID NO: 2.

17. The method of claim 14, wherein least one of the amino acids that has been changed is at position 212 of SEQ ID NO: 2.

18. The method of claim 14, wherein said protein is introduced into the host cell in step (b) by electroporation.

19. The method of claim 18, wherein the transposon that contains the transgene is introduced into the host cell in step (b) before said protein.

20. The method of claim 14, wherein the variant transposase is soluble in a low-salt electroporation buffer at a concentration of 20 mg/mL.

21. The method of claim 1, wherein said protein is degraded within 48 hours from when it is introduced into the host cell, thereby rapidly clearing transposase activity from the host cell.

22. The method of claim 1, wherein insertion efficiency of the transgene into the genome is dose dependent on the amount of said protein introduced into the cell, whereby the number of insertions per genome and the number of positive clones obtained can be controlled.

23. The method of claim 14, wherein the transgene encodes a chimeric antigen receptor (CAR).

24. The method of claim 14, wherein a product obtained according to the method is configured for administration into a human subject in need thereof.

* * * * *

SEQUENCE LISTING

```
Sequence total quantity: 34
SEQ ID NO: 1            moltype = AA  length = 340
FEATURE                 Location/Qualifiers
REGION                  1..340
                        note = hsSB
source                  1..340
                        mol_type = protein
                        organism = synthetic construct
SEQUENCE: 1
MGKSKEISQD LRKRIVDLHK SGSSLGAISK RLAVPRSSVQ TIVRKYKHHG TTQPSYRSGR    60
RRVLSPRDER TLVRKVQINP RTTAKDLVKM LEETGTKVSI STVKRVLYRH NLKGHSARKK   120
PLLQNRHKKA RLRFATAHGD KDRTFWRNVL WSDETKIELF GHNDHRYVWR KKGEASKPKN   180
```

```
TIPTVKHGGG SIMLWGCFAA GGTGALHKID GSMDAVQYVD ILKQHLKTSV RKLKLGRKWV     240
FQHDNDPKHT SKVVAKWLKD NKVKVLEWPS QSPDLNPIEN LWAELKKRVR ARRPTNLTQL     300
HQLCQEEWAK IHPNYCGKLV EGYPKRLTQV KQFKGNATKY                          340

SEQ ID NO: 2            moltype = AA   length = 340
FEATURE                 Location/Qualifiers
REGION                  1..340
                        note = non mutated SB100X
source                  1..340
                        mol_type = protein
                        organism = synthetic construct
SEQUENCE: 2
MGKSKEISQD LRKRIVDLHK SGSSLGAISK RLAVPRSSVQ TIVRKYKHHG TTQPSYRSGR     60
RRVLSPRDER TLVRKVQINP RTTAKDLVKM LEETGTKVSI STVKRVLYRH NLKGHSARKK    120
PLLQNRHKKA RLRFATAHGD KDRTFWRNVL WSDETKIELF GHNDHRYVWR KKGEACKPKN    180
TIPTVKHGGG SIMLWGCFAA GGTGALHKID GIMDAVQYVD ILKQHLKTSV RKLKLGRKWV    240
FQHDNDPKHT SKVVAKWLKD NKVKVLEWPS QSPDLNPIEN LWAELKKRVR ARRPTNLTQL    300
HQLCQEEWAK IHPNYCGKLV EGYPKRLTQV KQFKGNATKY                          340

SEQ ID NO: 3            moltype = AA   length = 343
FEATURE                 Location/Qualifiers
REGION                  1..343
                        note = hsSB for recombinant expression
source                  1..343
                        mol_type = protein
                        organism = synthetic construct
SEQUENCE: 3
GPMMGKSKEI SQDLRKRIVD LHKSGSSLGA ISKRLAVPRS SVQTIVRKYK HHGTTQPSYR     60
SGRRRVLSPR DERTLVRKVQ INPRTTAKDL VKMLEETGTK VSISTVKRVL YRHNLKGHSA    120
RKKPLLQNRH KKARLRFATA HGDKDRTFWR NVLWSDETKI ELFGHNDHRY VWRKKGEASK    180
PKNTIPTVKH GGGSIMLWGC FAAGGTGALH KIDGSMDAVQ YVDILKQHLK TSVRKLKLGR    240
KWVFQHDNDP KHTSKVVAKW LKDNKVKVLE WPSQSPDLNP IENLWAELKK RVRARRPTNL    300
TQLHQLCQEE WAKIHPNYCG KLVEGYPKRL TQVKQFKGNA TKY                      343

SEQ ID NO: 4            moltype = DNA   length = 27
FEATURE                 Location/Qualifiers
source                  1..27
                        mol_type = genomic DNA
                        organism = Homo sapiens
SEQUENCE: 4
tgtatatata tatatacagt tgaagtc                                         27

SEQ ID NO: 5            moltype = DNA   length = 27
FEATURE                 Location/Qualifiers
source                  1..27
                        mol_type = genomic DNA
                        organism = Homo sapiens
SEQUENCE: 5
gacacataca tacatacagt tgaagtc                                         27

SEQ ID NO: 6            moltype = DNA   length = 27
FEATURE                 Location/Qualifiers
source                  1..27
                        mol_type = genomic DNA
                        organism = Homo sapiens
SEQUENCE: 6
ctgttggatg cctctacagt tgaagtc                                         27

SEQ ID NO: 7            moltype = DNA   length = 27
FEATURE                 Location/Qualifiers
source                  1..27
                        mol_type = genomic DNA
                        organism = Homo sapiens
SEQUENCE: 7
gatatataca tatgtacagt tgaagtc                                         27

SEQ ID NO: 8            moltype = DNA   length = 27
FEATURE                 Location/Qualifiers
source                  1..27
                        mol_type = genomic DNA
                        organism = Homo sapiens
SEQUENCE: 8
gtactgagtg tatgtacagt tgaagtc                                         27

SEQ ID NO: 9            moltype = DNA   length = 27
FEATURE                 Location/Qualifiers
source                  1..27
                        mol_type = genomic DNA
                        organism = Homo sapiens
```

```
SEQUENCE: 9
ctttcaggaa caaatacagt tgaagtc                                              27

SEQ ID NO: 10           moltype = DNA   length = 28
FEATURE                 Location/Qualifiers
source                  1..28
                        mol_type = genomic DNA
                        organism = Homo sapiens
SEQUENCE: 10
tcaacttcag aaatgtacag ttgaagtc                                             28

SEQ ID NO: 11           moltype = DNA   length = 28
FEATURE                 Location/Qualifiers
source                  1..28
                        mol_type = genomic DNA
                        organism = Homo sapiens
SEQUENCE: 11
ggacacatac atacatacag ttgaagtc                                             28

SEQ ID NO: 12           moltype = DNA   length = 27
FEATURE                 Location/Qualifiers
source                  1..27
                        mol_type = genomic DNA
                        organism = Homo sapiens
SEQUENCE: 12
gtactgagtg tatgtacagt tgaagtc                                              27

SEQ ID NO: 13           moltype = DNA   length = 26
FEATURE                 Location/Qualifiers
source                  1..26
                        mol_type = genomic DNA
                        organism = Homo sapiens
SEQUENCE: 13
tttcaggaac aaatacagtt gaagtc                                               26

SEQ ID NO: 14           moltype = DNA   length = 27
FEATURE                 Location/Qualifiers
source                  1..27
                        mol_type = genomic DNA
                        organism = Homo sapiens
SEQUENCE: 14
actctcctat gatatacagt tgaagtc                                              27

SEQ ID NO: 15           moltype = DNA   length = 27
FEATURE                 Location/Qualifiers
source                  1..27
                        mol_type = genomic DNA
                        organism = Homo sapiens
SEQUENCE: 15
actctcctat gatatacagt tgaagtc                                              27

SEQ ID NO: 16           moltype = DNA   length = 27
FEATURE                 Location/Qualifiers
source                  1..27
                        mol_type = genomic DNA
                        organism = Homo sapiens
SEQUENCE: 16
aataatgcta gttatacagt tgaagtc                                              27

SEQ ID NO: 17           moltype = DNA   length = 27
FEATURE                 Location/Qualifiers
source                  1..27
                        mol_type = genomic DNA
                        organism = Homo sapiens
SEQUENCE: 17
atggcgagtt aacatacagt tgaagtc                                              27

SEQ ID NO: 18           moltype = DNA   length = 27
FEATURE                 Location/Qualifiers
source                  1..27
                        mol_type = genomic DNA
                        organism = Homo sapiens
SEQUENCE: 18
tattccatgg catatacagt tgaagtc                                              27

SEQ ID NO: 19           moltype = DNA   length = 27
FEATURE                 Location/Qualifiers
source                  1..27
                        mol_type = genomic DNA
```

```
                              -continued
                             organism = Homo sapiens
SEQUENCE: 19
tatagctaac aatatacagt tgaagtc                                              27

SEQ ID NO: 20         moltype = DNA  length = 26
FEATURE               Location/Qualifiers
source                1..26
                      mol_type = genomic DNA
                      organism = Homo sapiens
SEQUENCE: 20
gcaagtcctg tcatacagtt gaagtc                                               26

SEQ ID NO: 21         moltype = DNA  length = 27
FEATURE               Location/Qualifiers
source                1..27
                      mol_type = genomic DNA
                      organism = Homo sapiens
SEQUENCE: 21
ttaaatggaa taattacagt tgaagtc                                              27

SEQ ID NO: 22         moltype = DNA  length = 27
FEATURE               Location/Qualifiers
source                1..27
                      mol_type = genomic DNA
                      organism = Homo sapiens
SEQUENCE: 22
gacacataca tacatacagt tgaagtc                                              27

SEQ ID NO: 23         moltype = DNA  length = 27
FEATURE               Location/Qualifiers
source                1..27
                      mol_type = genomic DNA
                      organism = Homo sapiens
SEQUENCE: 23
aaagcaatag cacatacagt tgaagtc                                              27

SEQ ID NO: 24         moltype = DNA  length = 27
FEATURE               Location/Qualifiers
source                1..27
                      mol_type = genomic DNA
                      organism = Homo sapiens
SEQUENCE: 24
ttgtataaat catatacagt tgaagtc                                              27

SEQ ID NO: 25         moltype = DNA  length = 27
FEATURE               Location/Qualifiers
source                1..27
                      mol_type = genomic DNA
                      organism = Homo sapiens
SEQUENCE: 25
tatagctaac aatatacagt tgaagtc                                              27

SEQ ID NO: 26         moltype = DNA  length = 27
FEATURE               Location/Qualifiers
source                1..27
                      mol_type = genomic DNA
                      organism = Homo sapiens
SEQUENCE: 26
cctaatcatc tacttacagt tgaagtc                                              27

SEQ ID NO: 27         moltype = DNA  length = 27
FEATURE               Location/Qualifiers
source                1..27
                      mol_type = genomic DNA
                      organism = Homo sapiens
SEQUENCE: 27
ttgtataaat catatacagt tgaagtc                                              27

SEQ ID NO: 28         moltype = DNA  length = 27
FEATURE               Location/Qualifiers
source                1..27
                      mol_type = genomic DNA
                      organism = Homo sapiens
SEQUENCE: 28
catgtcacat gaagtacagt tgaagtc                                              27

SEQ ID NO: 29         moltype = DNA  length = 27
FEATURE               Location/Qualifiers
source                1..27
```

```
                        mol_type = genomic DNA
                        organism = Homo sapiens
SEQUENCE: 29
agtgaggttt aacatacagt tgaagtc                                         27

SEQ ID NO: 30           moltype = DNA   length = 27
FEATURE                 Location/Qualifiers
source                  1..27
                        mol_type = genomic DNA
                        organism = Homo sapiens
SEQUENCE: 30
ctattttgga aacatacagt tgaagtc                                         27

SEQ ID NO: 31           moltype = DNA   length = 54
FEATURE                 Location/Qualifiers
source                  1..54
                        mol_type = genomic DNA
                        organism = Homo sapiens
SEQUENCE: 31
catgtcacat gaagtacagt tgaagtcgac ttcaactgta cattaggtaa ccac            54

SEQ ID NO: 32           moltype = DNA   length = 55
FEATURE                 Location/Qualifiers
source                  1..55
                        mol_type = genomic DNA
                        organism = Homo sapiens
SEQUENCE: 32
attgtataaa tcatatacag ttgaagtcga cttcaactgt atctacatat tcata           55

SEQ ID NO: 33           moltype = DNA   length = 54
FEATURE                 Location/Qualifiers
source                  1..54
                        mol_type = genomic DNA
                        organism = Homo sapiens
SEQUENCE: 33
tcttttgttg catatacagt tgaagtcgac ttcaactgta tgtatgcatt tctg            54

SEQ ID NO: 34           moltype = DNA   length = 54
FEATURE                 Location/Qualifiers
source                  1..54
                        mol_type = genomic DNA
                        organism = Homo sapiens
SEQUENCE: 34
ccctctccta cacatacagt tgaagtcgac ttcaactgta cattatacta ctaa            54
```